United States Patent
Arnold et al.

(10) Patent No.: US 10,280,472 B2
(45) Date of Patent: *May 7, 2019

(54) SYSTEMS AND METHODS FOR GENOTYPING SEED COMPONENTS

(71) Applicant: PIONEER HI BRED INTERNATIONAL INC, Johnston, IA (US)

(72) Inventors: Randal Arnold, Ankeny, IA (US); Matthew Paul Cope, Johnston, IA (US); Justin Andrew Schares, Ames, IA (US); Yue Yun, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 326 days.

This patent is subject to a terminal disclaimer.

(21) Appl. No.: 14/730,271

(22) Filed: Jun. 4, 2015

(65) Prior Publication Data

US 2016/0060714 A1    Mar. 3, 2016

Related U.S. Application Data

(63) Continuation-in-part of application No. 14/473,114, filed on Aug. 29, 2014.

(51) Int. Cl.
*C12Q 1/6806* (2018.01)
*C12Q 1/6895* (2018.01)

(52) U.S. Cl.
CPC ......... *C12Q 1/6895* (2013.01); *C12Q 1/6806* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 7,935,529 B2 | 5/2011 | Davis et al. | |
| 8,119,342 B2* | 2/2012 | Van Dun | A01H 1/04 435/6.1 |
| 8,535,877 B2 | 9/2013 | Cope et al. | |
| 9,706,723 B2 | 7/2017 | Arnold et al. | |
| 2002/0188965 A1 | 12/2002 | Zhao | |
| 2005/0202573 A1 | 9/2005 | Koyata | |
| 2007/0204366 A1 | 8/2007 | Deppermann | |
| 2008/0131924 A1 | 6/2008 | Cope | |
| 2009/0215060 A1 | 8/2009 | Deppermann et al. | |
| 2010/0167376 A1 | 7/2010 | Hogan et al. | |
| 2010/0184152 A1 | 7/2010 | Sandler et al. | |
| 2015/0191771 A1* | 7/2015 | Bullock | A01H 1/04 800/320.1 |
| 2015/0285713 A1 | 10/2015 | Hunter | |
| 2016/0060715 A1 | 3/2016 | Arnold et al. | |
| 2016/0360716 A1 | 12/2016 | Arnold et al. | |
| 2017/0273297 A1 | 9/2017 | Arnold et al. | |

FOREIGN PATENT DOCUMENTS

| | | |
|---|---|---|
| WO | 2007/103786 A2 | 9/2007 |
| WO | 2011/019863 A1 | 2/2011 |
| WO | 2011/119763 A1 | 9/2011 |
| WO | 2014/195199 A1 | 12/2014 |
| WO | 2015/104358 A1 | 7/2015 |

OTHER PUBLICATIONS

Jain (Plant Cell Rep 2006 25:81-84).*
Zhou (Euphytica 2002 128:27-34).*
Bareja et al. The Parts of a Seed and Their Functions in Seed and Plant Development Nov. 2011 found online at http://www.cropsreview.com/parts-of-a-seed.html and downloaded Sep. 21, 2017).*
De Vogel "The Seedling" In: Seedlings of Dicotyledons, Centre for Agricultural Publishing and Documentation, Wageningen, Netherlands, pp. 9-25, 1983.*
S. Alasaad et al., HotSHOT Plus ThermalSHOCK, a new and efficient technique for preparation of PCR-quality mite genomic DNA, Parasitol Res, 2008, pp. 1455-1457, vol. 103.
DNeasy Plant Handbook, Qiagen, Oct. 2012.
Shibin Gao et al., Development of a seed DNA-based genotyping system for marker-assisted selection in maize, Mol Breeding, 2008, pp. 477-494, vol. 22.
N. Papazova et al., DNA extractability from the maize embryo and endosperm—relevance to GMO assessment in seed samples, Seed Sci & Tehnol, 2005, pp. 533-542, vol. 33.
Nath, Ujjal Kumar et al., Early, non-destructive selection of microspore-derived embryo genotypes in oilseed rape (*Brassica napus* L.) by molecular markers and oil quality analysis, Mol. Breeding, 2007, vol. 19(3):285-289.
Horn, Peggy et al., "Non-Destructive RAPD Genetic Diagnostics of Microspore-Derived Brassica Embryos", Plant Molecular Biology Reporter, 1992, vol. 10(3)285-293.
The International Search Report and Written Opinion of the International Searching Authority for PCT/US2015/034145, dated Aug. 27, 2015.

* cited by examiner

*Primary Examiner* — Amanda Haney

(57) ABSTRACT

Methods for obtaining genetic material from plant embryos while preserving their viability as well as methods for performing a molecular analysis of plant embryos, particularly with small quantities of genetic material by collecting shed cellular material from one or more plant embryos; obtaining DNA from the shed cellular material; performing a molecular analysis of the DNA; and germinating at least one of the one or more plant embryos. A further extension includes determining whether to germinate and grow the embryo or to discard the embryo based on its genotype as part of a breeding process. Also provided are methods of genotyping embryos using embryo shed cellular material contained in or on agar and methods of analyzing plant embryonic tissue derived from microspores.

6 Claims, 17 Drawing Sheets

Figure 4 Endpoint Fluorescence Scatter Plot

Figure 5 Endpoint Fluorescence Scatter Plot

Figure 8 Endpoint
Fluorescence Scatter Plot

FIGURE 14
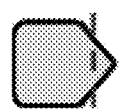
a)
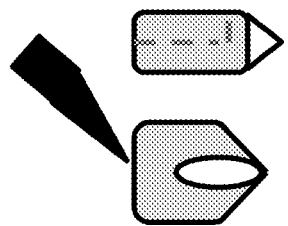
b)
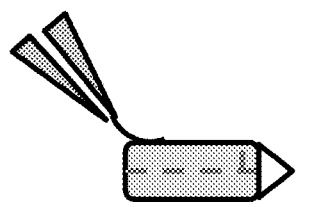
c)

SYSTEMS AND METHODS FOR GENOTYPING SEED COMPONENTS

CROSS REFERENCE TO RELATED APPLICATIONS

This application is a Continuation-in-Part of U.S. National application Ser. No. 14/473,114, filed Aug. 29, 2014, which is incorporated by reference in its entirety.

BACKGROUND

Present conventional seed analysis methods used in genetic, biochemical, or phenotypic analysis, require at least a part of the seed to be removed and processed. In removing some seed tissue, various objectives may need to be met. These may include one or more of the following objectives:

(a) maintain seed viability after collection of seed tissue, if required.

(b) obtain at least a minimum required amount of tissue, without affecting viability.

(c) obtain tissue from a specific location on the seed, often requiring the ability to orient the seed in a specific position.

(d) maintain a particular throughput level for efficiency purposes.

(e) reduce or virtually eliminate contamination.

(f) allow for the tracking of separate tissues and their correlation to seeds from which the tissues were obtained.

Conventional seed testing technologies do not address these requirements sufficiently, resulting in pressures on capital and labor resources, and thus illustrate the need for an improvement in the state of the art. The current methods are relatively low throughput, have substantial risk of cross-contamination, and tend to be inconsistent because of a reliance on significant manual handling, orienting, and removal of the tissue from the seed. This can affect the type of tissue taken from the seed and the likelihood that the seed will germinate. There is a need to eliminate the resources current methods require for cleaning between removal of individual portions of seed tissue. There is also a need to reduce or minimize cross-contamination between unique tissue portions to be tested by carry-over or other reasons, or any contamination from any source of any other tissue. Furthermore, there is a need for more reliability and accuracy.

In addition, some of the objectives presented above can be conflicting and even antagonistic. For example, obtaining a useful amount of tissue while maintaining seed viability requires taking some seed tissue, but not too much. Moreover, high-throughput methodologies involve rapid operations but may be accompanied by decreases in accuracy and increased risk of contamination, such that the methods must be done more slowly than is technically possible in order to overcome the limitations. These multiple objectives have therefore existed in the art and have not been satisfactorily addressed or balanced by the currently available methods and apparatuses. There is a need in the art to overcome the above-described types of problems such that the maximum number of objectives is realized.

SUMMARY

The invention includes methods for analyzing plant material, while preserving the viability of the plant material (i.e. ability to form a plant). The method may include the steps of collecting shed cellular material from one or more plant embryos (or from plant embryonic tissue derived from microspores); obtaining genetic material such as DNA from the shed cellular material; and performing a molecular analysis of the genetic material. The methods may further include germinating at least one of said one or more plant embryos. An embryo may be obtained from a seed or may be derived from other tissues through somatic or gametic (microspore) embryogenesis. In one embodiment, the shed cellular material is collected from an embryo by agitating the embryo in a non-destructive medium such as water or other aqueous solution. Agitation may occur by any means known to one of ordinary skill in the art.

In another embodiment, shed cellular material of a plant embryo is collected by obtaining a portion of agar in contact with a plant embryo, wherein said portion comprises shed cellular material of the plant embryo. The portion of agar may be placed in a non-destructive medium consisting essentially of water or TE, and agitation may be applied using any means known to one of ordinary skill in the art. The methods may further include removing the embryo from the agar and either storing the embryo using methods provided herein or transferring the embryo to germination medium. The plant embryo may be a haploid embryo, and the agar may include a chromosome doubling agent such as but not limited to colchicine. As such, the plant embryo may become a doubled haploid. In another embodiment, filter paper may be used in lieu of the agar.

In any of the methods above, DNA may be obtained from the shed cellular material by exposing the collected shed cellular material to cold and then heat followed by agitation; the steps may be repeated. In other embodiments, DNA may be obtained from the shed cellular material by heating of the shed cellular material and agitation; the steps may be repeated. In other embodiments, DNA may be obtained by incubating the shed cellular material with an enzyme; the enzyme may be VISCOZYME® L, a multi-enzyme complex containing a wide range of carbohydrases, including arabanase, cellulase, β-glucanase, hemicellulase, and xylanase. (See the Sigma Aldrich product catalog). In still other embodiments, DNA may be obtained using DNA extraction techniques, such as but not limited to the use of magnetic particles that bind genetic material or any method known to one of ordinary skill in the art.

Methods include obtaining genetic material from shed cellular material of embryos (or embryonic tissue derived from microspores) and performing a molecular analysis of the genetic material while preserving the embryos' ability to germinate. The molecular analysis may be genotyping, which may occur by way of: single nucleotide polymorphism detection, restriction fragment length polymorphism identification, random amplified polymorphic detection, amplified fragment length polymorphism detection, polymerase chain reaction, DNA sequencing, whole genome sequencing, allele specific oligonucleotide probes, or DNA hybridization to DNA microarrays or beads. Whole genome amplification may be performed prior to the molecular analysis. In other embodiments, one or more of the steps may be automated.

In some embodiments, embryos may be stored by suspending the embryos or embryonic tissue in an aqueous solution surrounded by a matrix of one or more oils. Preferably, at least one of the one or more oils has a density greater than that of the aqueous solution. Storage of the embryos or embryonic tissue may occur before or after collection of shed cellular material from the embryo or embryonic tissue. In some aspects, antimicrobial agents and/or minimal growth media may be added to the aqueous solution. In other aspects, the embryos or embryonic tissue may be stored in cold (preferably 4° C.) and/or dark conditions to prevent premature germination. In some embodiments, the embryos or embryonic tissue may be transferred for continued storage. In other embodiments, the embryos may be transferred to germination medium, and one or more of the embryos may be germinated. In still other embodiments, an aliquot of the aqueous solution may be removed, genetic material may be obtained from cellular material in the aliquot, and the genetic material may be used for molecular analysis (e.g. to genotype the stored embryos). The molecular analysis may be genotyping, which may occur by way of: single nucleotide polymorphism detection, restriction fragment length polymorphism identification, random amplified polymorphic detection, amplified fragment length polymorphism detection, polymerase chain reaction, DNA sequencing, whole genome sequencing, allele specific oligonucleotide probes, or DNA hybridization to DNA microarrays or beads. In other embodiments, one or more of the steps described above may be automated.

Methods include obtaining embryonic DNA (whether or not said obtaining the embryonic DNA includes extraction), storing the embryo from which the DNA was extracted in a manner that preserves the embryo's ability to germinate and grow into a plant, genotyping the embryo using the embryonic DNA, and determining whether to germinate and grow the embryo (i.e. selecting) or to discard the embryo based on its genotype (i.e. counterselecting). An embryo that is selected to germinate and grow based on its genotype may be grown into a plant and phenotyped, used for breeding, or used to bulk up seed of the same genotype. In preferred embodiments, one or more steps of the method may be automated.

One embodiment allows for determining the maternal lineage of one or more seeds by collecting maternal seed tissue from the one or more seeds; washing the maternal seed tissue; dissociating and homogenizing the maternal seed tissue to obtain a homogenized solution; centrifuging the homogenized solution to obtain supernatant; and performing a molecular analysis using supernatant DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The dissociating and breaking pericarp tissue may be performed using a cell dissociator (such as gentleMACS™, Miltenyi Biotech). The method may further comprise using whole genome amplification prior to the molecular analysis to obtain sufficient DNA yield.

Another embodiment allows for determining the maternal lineage of one or more seeds by collecting maternal seed tissue from the one or more seeds; washing the maternal seed tissue; dissociating and homogenizing the maternal seed tissue to obtain a homogenized solution; extracting DNA from cells contained within the homogenized solution; and performing a molecular analysis of the extracted DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The dissociating and homogenizing step may be performed using a cell dissociator (such as gentleMACS™, Miltenyi Biotech). The extracting step may be performed using DNA-binding magnetic particles or Extract-N-Amp™. The method may further comprise using whole genome amplification prior to the molecular analysis to obtain sufficient DNA yield.

Another embodiment allows for determining the maternal lineage of one or more seeds by collecting maternal seed tissue from the one or more seeds; washing the maternal seed tissue; disrupting the maternal seed tissue in liquid nitrogen; extracting DNA from the disrupted maternal seed tissue; and performing a molecular analysis of the extracted DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The extracting step may be performed using DNA-binding magnetic particles or Extract-N-Amp™. The method may further comprise using whole genome amplification prior to the molecular analysis to obtain sufficient DNA yield.

Another embodiment allows for determining the maternal lineage of one or more seeds by collecting maternal seed tissue from the one or more seeds; washing the maternal seed tissue; extracting DNA directly from the washed maternal seed tissue; and performing a molecular analysis of the extracted DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The extracting step may be performed using Extract-N-Amp™. The method may further comprise using whole genome amplification prior to the molecular analysis to obtain sufficient DNA yield.

In any of the embodiments stated above, the molecular analysis may be genotyping. When maternal seed tissue from more than one seed replicate is collected, a consensus genotype may be obtained.

DESCRIPTIONS OF THE DRAWINGS

In FIGS. 1 through 11, upside down triangles represent samples having one homozygous state; right side up triangles represent samples having the other homozygous state; triangles pointing towards the left represent the heterozygous control; circles represent missing or negative control data; and diamonds represent unquantifiable calls. The tighter the cluster of points along a line parallel to either axis, the less variation there is with the method being tested.

Figure 11:
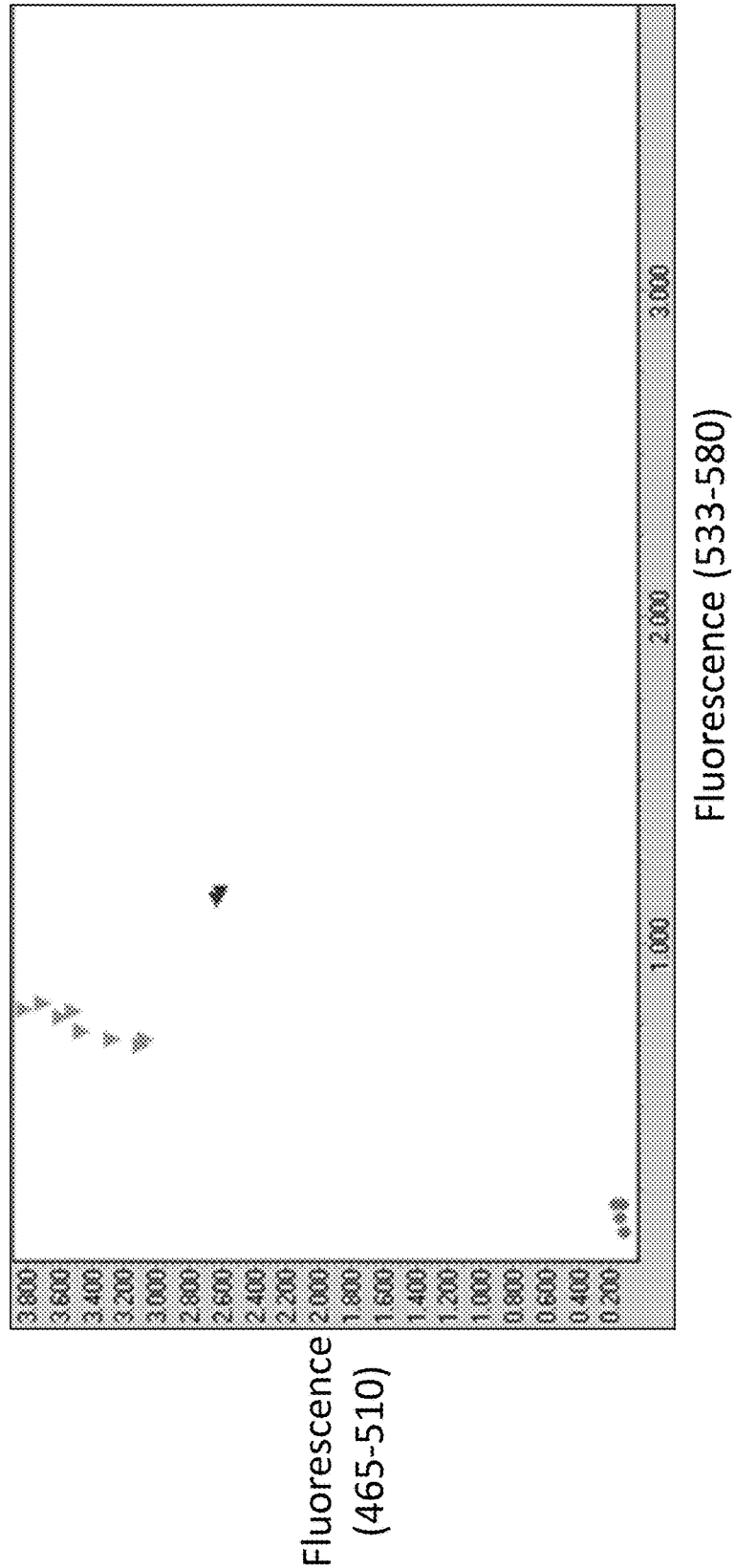

FIG. 11 depicts genotyping data from one marker using DNA obtained with the cold-heat shock treatment and whole genome amplification (using the REPLI-g Single Cell Kit) to obtain sufficient yield of DNA prior to genotyping. The data represents four treatments (incubate only; vortex at speed 3 for 5 seconds; vortex at speed 10 for 5 seconds; and vortex at speed 10 for 30 seconds) in an incubation volume of 10 μL.

Figure 12:
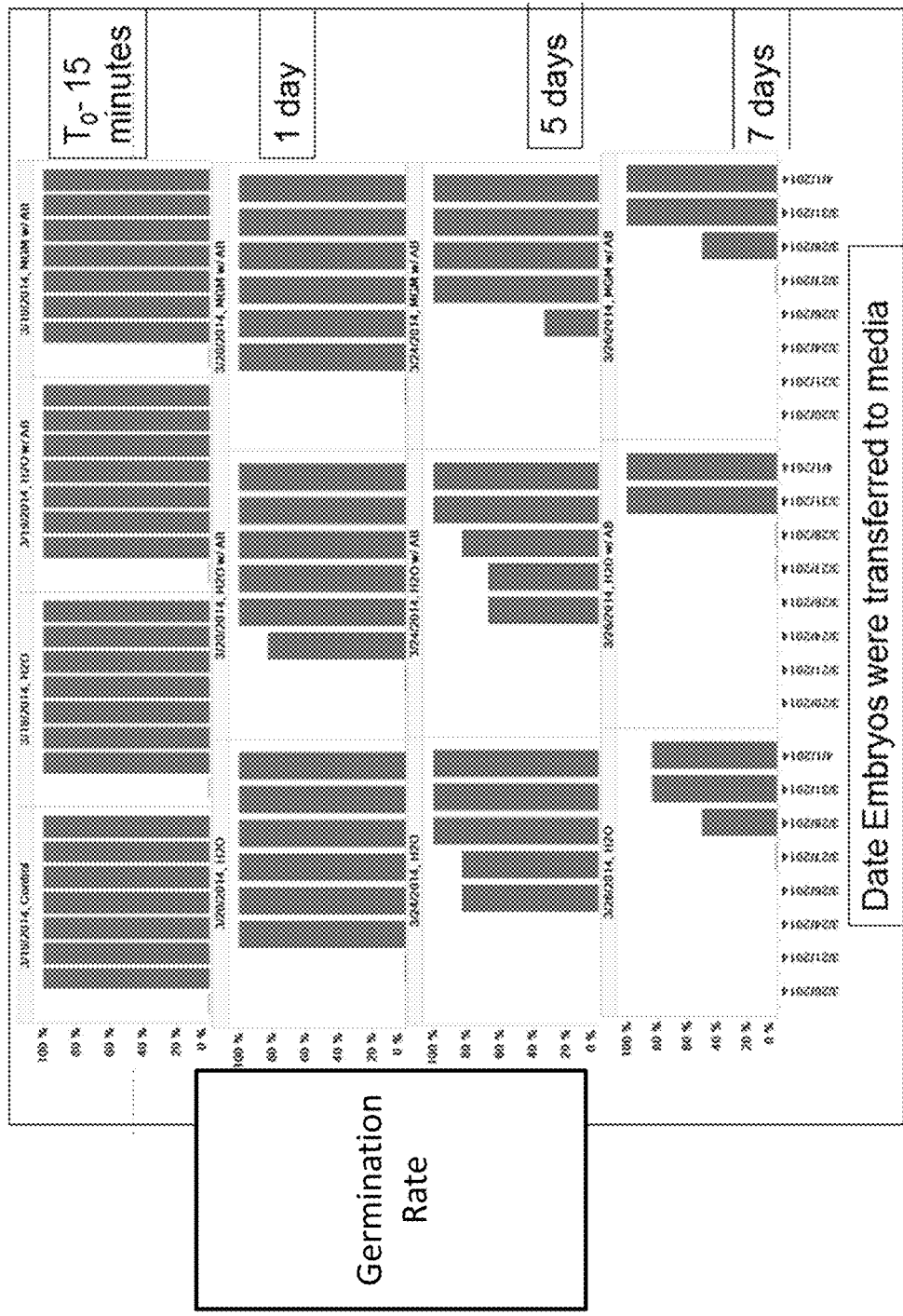

FIG. 12 depicts germination results for embryos of a first maize line, wherein the embryos were stored using methods provided herein.

Figure 13:
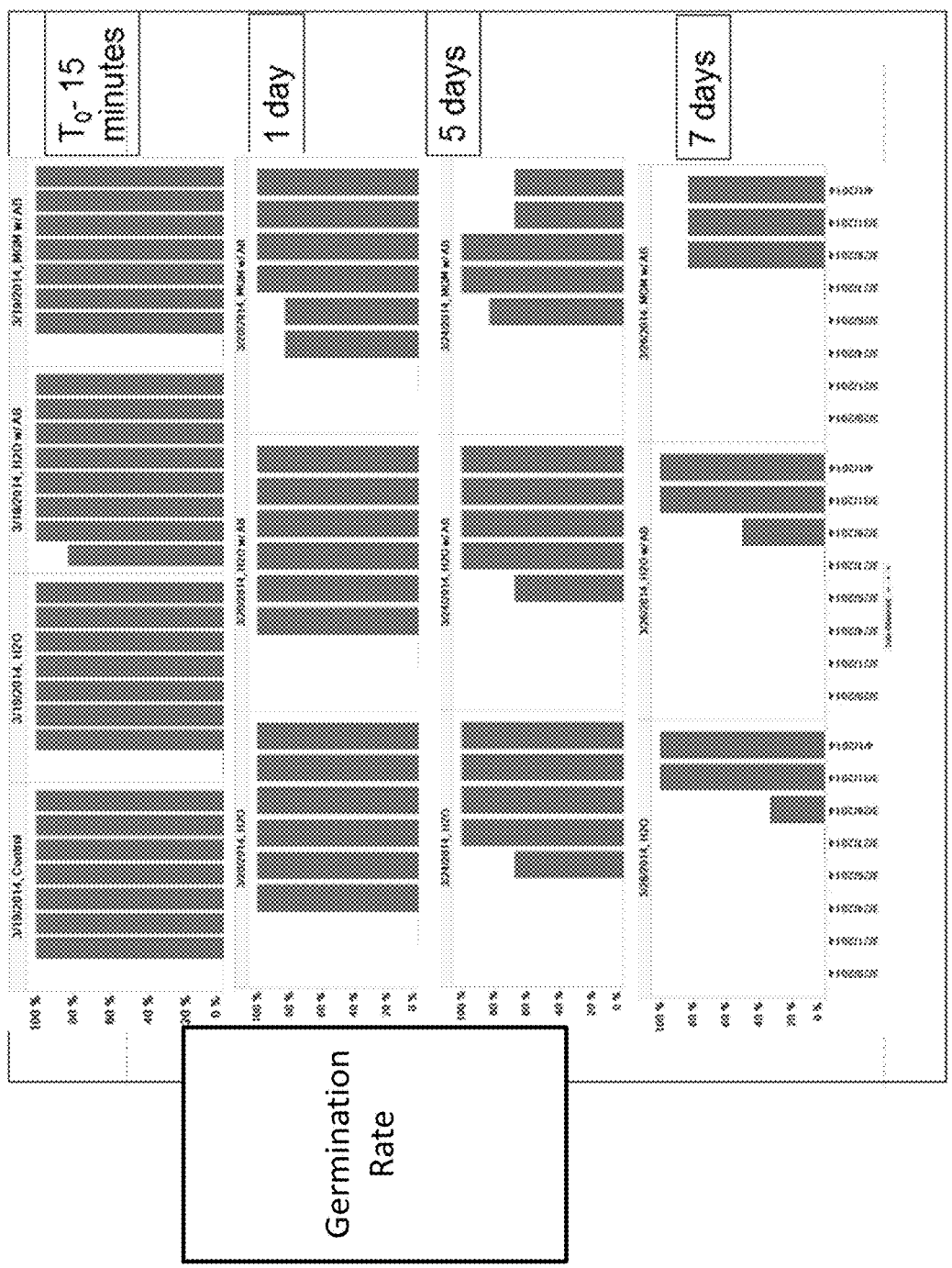

FIG. 13 depicts germination results for embryos of a second maize line, wherein the embryos were stored using methods provided herein.

FIG. 14 depicts the steps involved in peeling of pericarp tissue.

Figure 15:
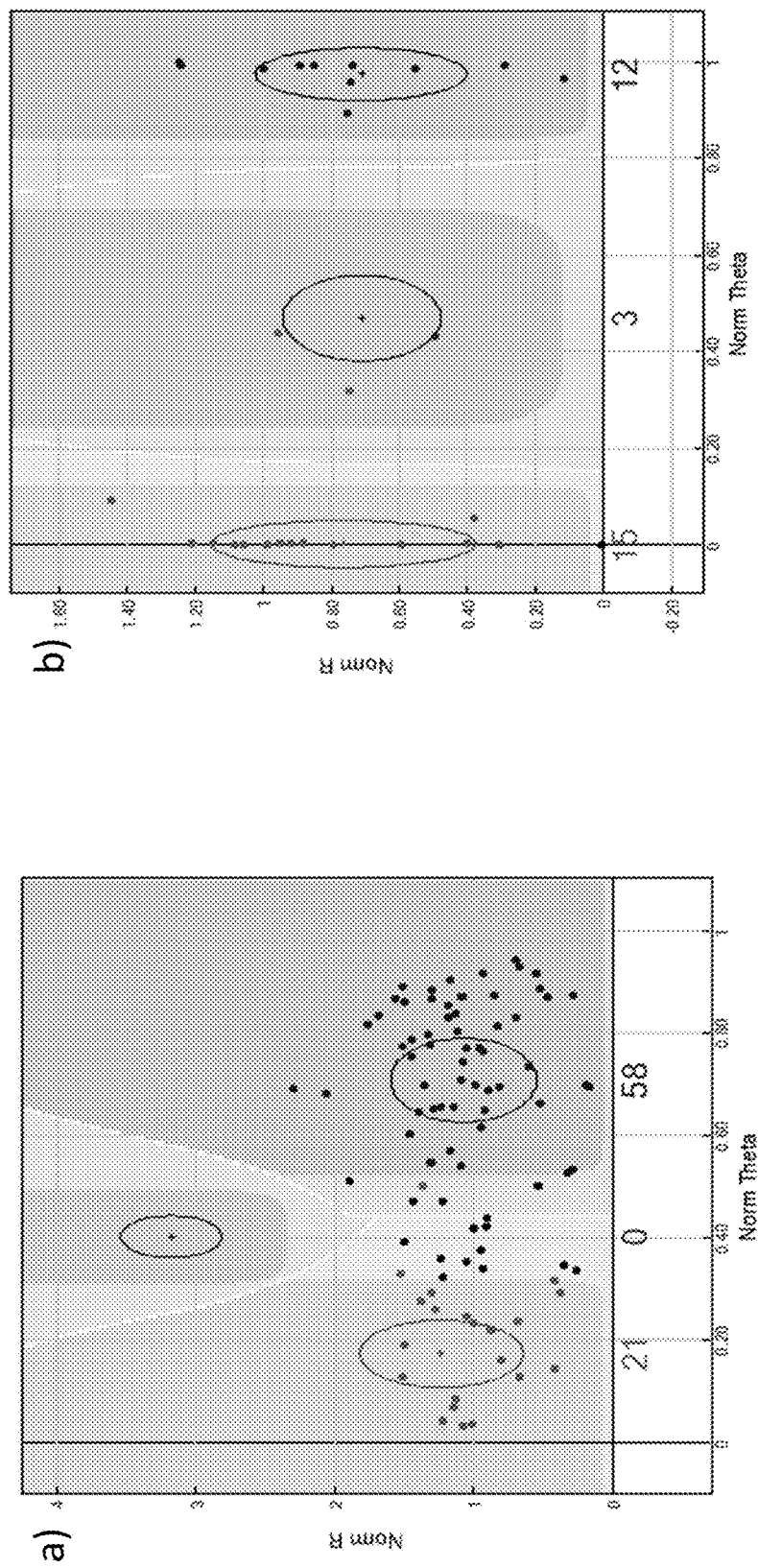

FIG. 15 compares the ILLUMINA® GOLDENGATE® Genotyping Assay using DNA obtained from a) conventional CTAB DNA extraction method using multiple seeds and b) SBEADEX® DNA extraction method using one seed (with tissue wash) followed by the whole genome amplification.

Figure 16:
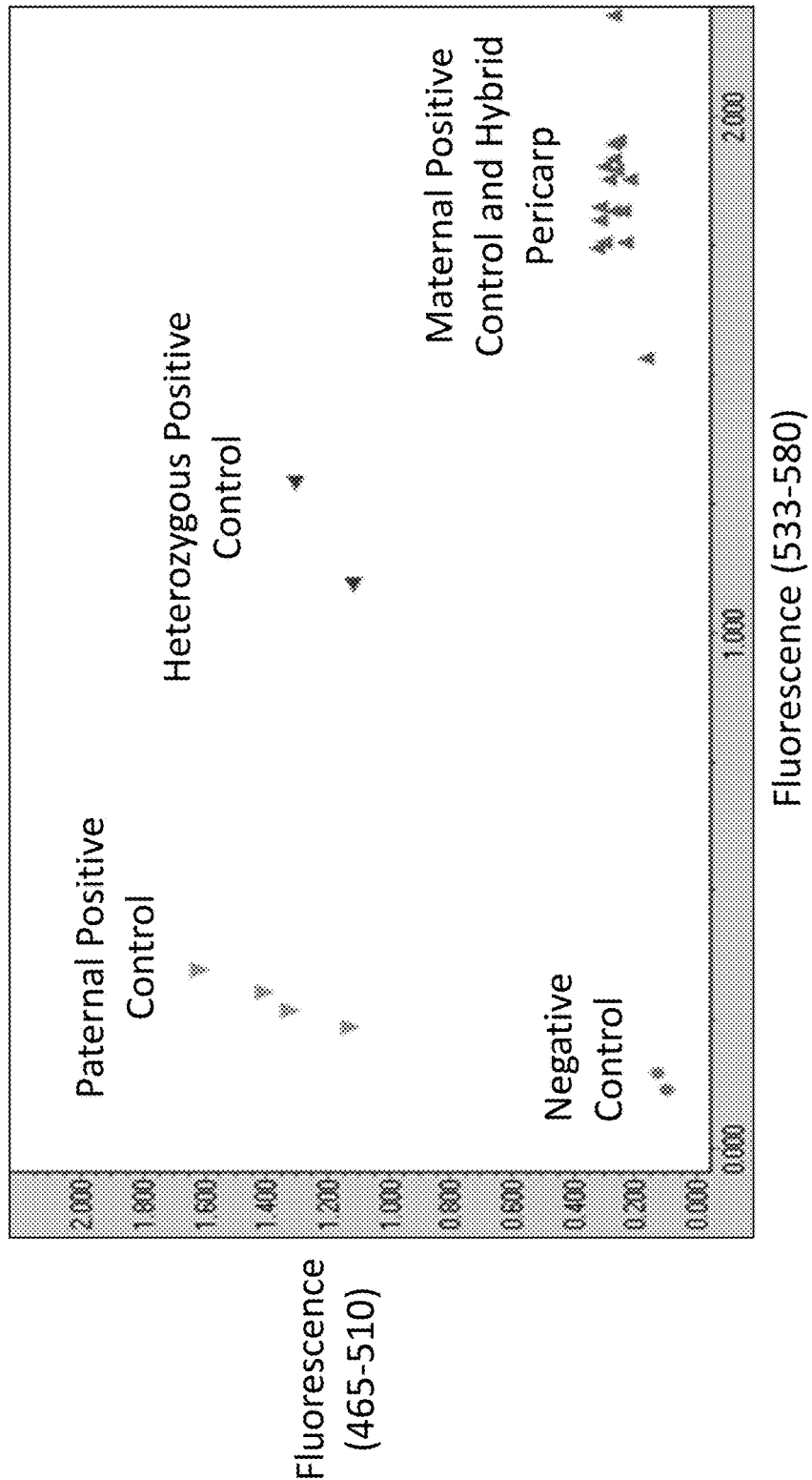

FIG. 16 demonstrates that quality fluorescent marker data can be obtained from a single pericarp.

Figure 17:
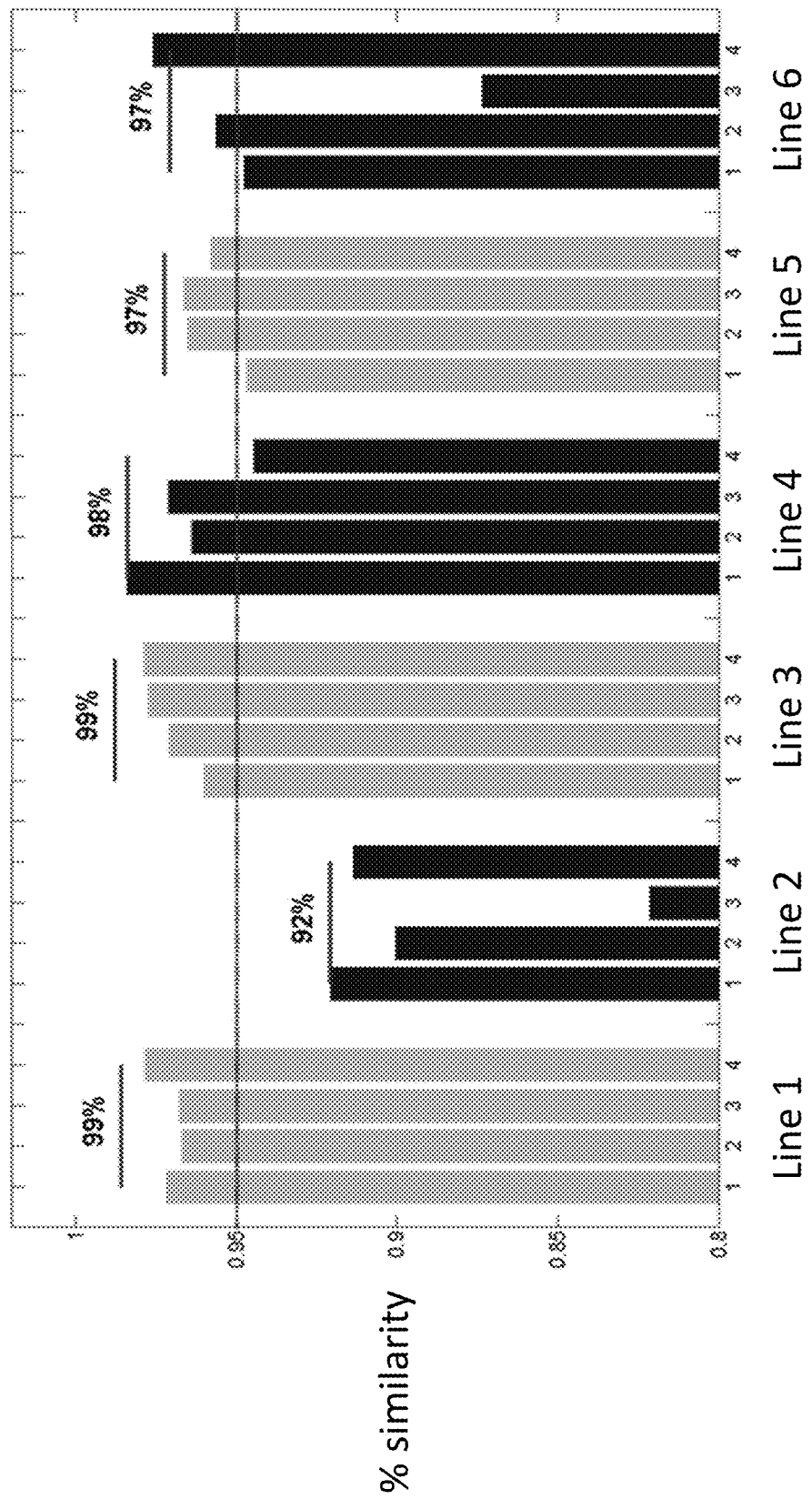

FIG. 17 demonstrates the high degree of similarity between the measured genotype of the pericarp tissue extracted from a single seed (each line) and the known maternal genotype.

DETAILED DESCRIPTION OF PREFERRED EMBODIMENTS

Genotyping of embryos or embryonic tissue permits molecular characterization early in plant development, allowing selections of a desired genotype to be made weeks or months earlier than other methods such as with phenotyping or plant genotyping. Consequently, resources can be focused earlier on embryos that have the highest probability of developing into desirable plants. Techniques for genetically characterizing embryonic tissue can greatly enhance a molecular breeding program and eliminate a great deal of effort and resources by allowing breeders to only grow plants with the desired genetics. Furthermore, the ability to reliably genetically characterize an embryo without impeding its ability to germinate can substantially reduce the amount of time required between generations of plants.

Non-destructive genotyping in a plant breeding program may require one or more of the following steps:
1. Separating viable plant sources from other plant material;
2. Preserving the viable plant sources;
3. Obtaining genetic material corresponding to multiple viable plant sources while maintaining the viability of the multiple viable plant sources;
4. Obtaining genetic material for molecular characterization;
5. Molecularly characterizing the genetic material from the multiple viable plant sources;
6. Selecting one or more viable plant sources based on molecular characterizations; and
7. Growing the selected viable plant sources.

The viable plant sources may be seeds, plant embryos, plant tissue, or whole plants, for example. Most typically, viable plant sources are capable of being grown into plants, although not necessarily. The genetic material may be crude, i.e., mixed with other portions of plant tissue including cellulosic and protein materials, or it may be purified (such as, for example, by DNA extraction methods known to one of ordinary skill in the art). The genetic material may be taken directly from the viable plant sources, or it may be taken from other plant material. The preserving step may include keeping the viable plant sources in a manner that preserves an ability to be grown into a plant. The preserving step may include keeping the viable plant sources in a manner that prevents germination. The molecularly characterizing step may involve genotyping, genetic sequencing, RNA sequencing, restriction fragment length polymorphism marker detection, single nucleotide polymorphism detection, whole genome amplification, specific protein detection, oil content measurement, protein content measurement, or any other molecular analysis that may serve as a basis to select or reject particular viable plant sources. The growing step may involve any means of growing plants, including planting in a field or a greenhouse, growing hydroponically, growing aeroponically, or any other method of growing a plant. In some embodiments, the plant is grown to maturity and produces pollen and/or seeds. In some embodiments, one or more of the steps is automated.

Separating Viable Plant Sources.

In one embodiment involving corn, the caps of corn kernels are sliced off while they are still attached to the corn cob. The caps of the corn kernels are typically the farthest part of the kernel from the embryo, which is closer to the tip of the kernel, which is attached to the cob. Each embryo may then be removed, for example, using a small spatula or any other suitable device. In one embodiment, this process is automated using a robot cap slicer, a robotically manipulated spatula, and a machine vision platform for precise cutting and embryo removal control.

In another embodiment, corn kernels may be removed from the cob before embryo removal. The kernels may then be oriented in the same way, for example, by floating the kernels in water or in a solution. The kernels may then be immobilized, while preserving their orientations, for example, by draining them into a container with multiple wells, each well holding an oriented kernel. Small pieces of the tips of the kernels may then be removed, preferably small enough to avoid damage to the embryos. The embryos may then be extracted by gently squeezing the kernels from the cap sides of the kernels.

Following embryo removal, each embryo may be placed in a container with multiple wells, wherein the location of each embryo in each well is recorded, associated, or correlated with the location of genetic material obtained in a subsequent step.

Preserving the Viable Plant Sources

When the viable plant sources are seeds, preservation of seeds for the quantity of time required to perform a molecular analysis typically requires no particular care. When the viable plant sources are embryos, however, special care should be taken to preserve viability. Embryos may be stored in a multiple well plate, where each well corresponds to a well in which extracted tissue to be tested is placed.

In one preferred method, embryos are suspended in an aqueous solution surrounded by a matrix of one or more oils. Oil having a density less than water will cover the embryo(s) in the aqueous solution, while oil having a density greater than water will support the embryo(s) in the aqueous solution. In some embodiments, the one or more plant embryos is suspended in an aqueous solution surrounded by a matrix of two or more oils, wherein at least one of the two or more oils is more dense than the aqueous solution and at least one of the two or more oils is less dense than the aqueous solution, further wherein the aqueous solution is surrounded by the oil that is more dense than the aqueous solution and the oil that is less dense than the aqueous solution. Storage of the embryos may occur before or after collection of cellular material from the embryo, any time after pollination if the embryo is obtained directly from a seed. In some embodiments, antimicrobial agents and/or minimal growth media may be added to the aqueous solution. In some embodiments, the embryos may be stored in cold and/or dark conditions to prevent premature germination. In a preferred embodiment, the embryos are stored at a temperature of approximately 4° C. In some embodiments, the embryos may be transferred for continued storage. In other embodiments, the embryos may be transferred to germination medium, and the embryos may be germinated. In a preferred embodiment, an aliquot of the aqueous solution may be removed; genetic material may be obtained from cellular material in the aliquot; and the genetic material may be used for molecular analysis (e.g. to genotype the stored embryos).

High density oil that may be used in this method includes but is not limited to perfluoro compounds having 12 compounds (e.g., DuPont's lower viscosity KRYTOX® oils). Low density oil that may be used in this method includes but is not limited to phenylmethylpolysiloxane. Other non-toxic oils known to those of ordinary skill in the art may be used instead of or in combination with these compounds.

Obtaining Cellular Material.

Cellular material refers to any plant material remaining after the separation of viable plant sources. Cellular material may include embryo and/or endosperm material and may refer to one cell, multiple cells, or cellular tissue. If genetic information for the parent plant is desired, genetic material may be obtained from the pericarp.

In one embodiment, the cellular material is from one or more plant embryos wherein the one or more plant embryos are obtained directly from a seed (i.e. zygotic embryogenesis) or may be "derived from other tissues" through somatic or gametic (microspore) embryogenesis. Somatic embryogenesis relates to embryogenesis arising from somatic cells (i.e. vegetative or non-gametic cells), namely from isolated somatic explants whereas gametic embryogenesis relates to embryogenesis arising from gametic cells (i.e. microspores). Since somatic and gametic cells are not naturally embryogenic, such cells must be induced to become embryogenic. Conversion to embryogenic cells may be achieved by external stimuli such as auxin, cytokinin, pH shifts, growth regulators, and heavy metal ions (Yeung, 1995 In: Thorpe T A (ed) *In Vitro Embryogenesis in Plants* (pp. 205-249; Dodeman et al. (1997) *J. Exp. Bot.* 48:1493-1509. Shed cellular material may be collected from embryonic tissue by agitating the embryo while it is in a non-destructive medium such as water or other aqueous solution. The non-destructive medium is any medium that allows the embryo to maintain its viability (i.e. its ability to grown into a normal plant). Agitation may occur by any means known to one of ordinary skill in the art.

In another embodiment, the cellular material is present in or on agar that is in contact with the plant embryo. A portion of agar may be placed in a non-destructive medium consisting essentially of water or TE buffer, and agitation may be applied using any means known to one of ordinary skill in the art. The methods may further include removing the plant embryo from the agar and either storing the plant embryo using methods provided herein or transferring the embryo to germination medium. The plant embryo may be a haploid embryo, and the agar may include a chromosome doubling agent such as but not limited to colchicine. As such, the plant embryo may become a doubled haploid. Similarly, cellular material may also be present on filter paper upon which the embryo is in contact. Thus, in another embodiment, filter paper may be used in lieu of the agar. One of ordinary skill in the art knows that DNA can be obtained from plant samples collected on filter paper.

In another embodiment, when a spatula (or any other implement or device used to excise a piece of the scutellum) is used to remove the embryo from a seed, the spatula may then be dipped into a well in one container that corresponds to a well in a second container that houses the embryo. Preferably, the spatula is dipped into a well containing an aqueous solution. When the spatula is used to remove the embryo, sufficient quantities of endosperm tissue remain on the spatula (i.e. shed cellular material), and the spatula need not contact the kernel from which the embryo was removed following embryo extraction. The spatula may be dipped in the well containing aqueous solution immediately after the embryo has been removed. If the same spatula is used for the removal of multiple embryos and/or endosperm tissue, it preferably will be cleaned between each use to remove any shed cellular material that could lead to contamination.

In another embodiment, the embryo(s) may optionally be washed, for example with water or culture medium, to remove any endosperm attached to the embryo. The washed embryo(s) may then be immersed in fresh water or other aqueous solution and agitated to remove a small number of embryo cells from the embryo(s) into the fresh water or other aqueous solution (i.e. shed cellular material). The embryo(s) may then be transferred to a container with multiple wells, and some or all of the fresh water or aqueous solution containing the small number of embryo cells may be transferred to a correlated well in a separate container with multiple wells.

In one embodiment, a small piece of the scutellum may be excised using any method known in the art, include cutting with a blade or a laser. Preferably, the piece of the scutellum is small enough so as not to compromise embryo viability. The embryo and corresponding piece of scutellum may then be placed in separate containers with wells, in which the well containing the embryo in the embryo container and the well containing the corresponding scutellum in the scutellum container are correlated such that any information gained from the scutellum is associated with the embryo from which the scutellum tissue was obtained.

In another embodiment not necessarily requiring embryo extraction or other separation of viable plant sources, a piece of the outer coat of a corn kernel, the pericarp, may be excised in order to conduct a molecular analysis of the parent plant. In this embodiment, kernels may be soaked in water before making cuts in the pericarp. The back side of the kernel (farthest from the embryo) may be cut with a sharp blade, as shown in FIG. 14a. Preferably, the blade is sterilized after the first cut before outer edge of the kernel may be cut with the sharp blade, starting from one end of the first cut, around the edge of the kernel, and down to the other end of the first cut, as shown in FIG. 14b. Sterilized forceps may be used to peel the pericarp tissue from the kernel as shown in FIG. 14c. While the cut can be made on the front side of the kernel (nearest the embryo), the cut is preferably made on the back side to reduce the possibility that the pericarp will be contaminated with endosperm tissue. To further reduce the possibility of contamination, the pericarp tissue may be washed after it is excised. The pericarp may be placed in the well of a container and the seed from which the pericarp was excised (or the embryo from that seed) may be placed in a corresponding well of a separate container. As will be understood by those of ordinary skill in the art, there are other comparable methods for isolating pericarp tissue, and in some embodiments of the invention, pericarp DNA may be extracted without pericarp removal.

The tissue to be analyzed is preferably associated or correlated with its corresponding viable plant source so that the corresponding viable plant source can be selected based on the results of the tissue analysis.

Obtaining Genetic Material for Molecular Characterization

In order for genetic material to be analyzed, it must be freed from the cell such that it is accessible for molecular analysis. This may involve physical treatments such as exposure to cold-heat or just heat, incubation with enzymes, or even DNA extraction techniques (although it is important to note that extraction is not a necessary step in obtaining DNA for molecular analysis). Essentially any process that disrupts the tissue and breaks open cells, thereby releasing DNA that can be used for molecular characterization, may be used in the methods provided herein.

In some embodiments, DNA may be obtained from the shed cellular material by exposing the collected shed cellular material to cold-heat or heat, agitating the mixture, and optionally repeating. In other embodiments, DNA may be obtained by incubating shed cellular material with an enzyme; the enzyme may be VISCOZYME® L, a multi-enzyme complex containing a wide range of carbohydrases, including arabanase, cellulase, β-glucanase, hemicellulase, and xylanase. (See the Sigma Aldrich product catalog). In still other embodiments, obtaining DNA may comprise extraction of the DNA, such as through the use of magnetic particles that bind genetic material or any method known to one of ordinary skill in the art. However, extraction is not necessary for obtaining DNA.

In other embodiments involving maternal seed tissue such as pericarp tissue, tissue may be dissociated using a cell dissociator (such as gentleMACS™, Miltenyi Biotech), optionally followed by DNA extraction. In another embodiment, the maternal seed tissue may be disrupted in liquid nitrogen prior to DNA extraction. In yet another embodiment, DNA may be extracted directly from washed maternal seed tissue (e.g. using Extract-N-Amp™).

Molecularly Characterizing the Genetic Material from the Multiple Viable Plant Sources In cases where the yield of DNA obtained from embryo tissue is not sufficient for some molecular analysis (e.g. high density genotyping), whole genome amplification techniques may be used. The Qiagen REPLI-g® kit, the Sigma-Aldrich SeqPlex kit, or any other technique known to one of ordinary skill in the art may be used to amplify DNA from embryo tissue.

Other useful molecular characterizations may involve sequencing all or part of the genome of the tissue extracted from the seed, or using molecular markers and fluorescent probes to genotype. Molecular characterization need not focus on the genotype of the extracted tissue, but instead may measure other properties such as oil content, oil composition, protein content, or the presence or absence of particular molecules in the tissue.

In a preferred embodiment, genetic material is placed in a well of a multiple well plate containing a bilayer of oil, one layer having a density greater than water and one layer having a density less than water. Multiple wells contain multiple different genetic materials. Fluorescently labeled probes are added to the genetic materials, and thermocycling to cause amplification and hybridization of the probes is performed in a multiple well plate. The wells are irradiated and fluorescence is detected from the labels to generate genotypic data. Alternatively, the genetic material may be sequenced, in whole or in part, in a multiple well plate.

Selecting One or More Viable Plant Sources Based on Molecular Characterizations

In a molecular breeding program, plants or potential plants are selected to participate in subsequent generations based on their genotype. Typically this involves determining whether the plant has inherited one or more desirable traits indicated by genetic markers whose presence or absence can be determined based on the genotyping. Plant breeders select those plants that have the desired traits to participate in further breeding, to inbreed, or as part of a process to create inbreds through haploid doubling techniques.

Growing the Selected Viable Plant Sources.

Those plants that are selected based on the presence of desirable traits as determined by their genotype may be grown into mature plants, to obtain haploid material to create a double haploid inbred, to breed with itself to create an inbred, or to breed with other plants to improve and diversify germplasm.

In one embodiment, a consensus genotype may be derived by considering genotypic data from multiple tissue specimens obtained from one or more seeds, each tissue specimen being a replicate. In a genotyping experiment that identifies multiple nucleotides across multiple positions in a genome, it is not uncommon for any particular experiment to fail to identify one or more of the nucleotides to be identified. Thus, missing nucleotide identifications for each missing position may be noted for each of the specimens. If nucleotide identification from only one specimen is available for a particular nucleotide position, then that nucleotide identification is assigned as the consensus data for that position. If two or more nucleotide identifications are available for a particular nucleotide position, then the majority of nucleotide identifications for that position is assigned as the consensus data for that position. If no majority identification exists for a position, that position is assigned as missing data for the consensus genotype. While the examples provided here relate to obtaining and genotyping tissues from a monocot, specifically maize, those of ordinary skill in the art would understand how to apply the same or similar methods to other monocots and dicots; the methods may be adapted to any plant. Further, the genotyping methods disclosed herein may be used to genotype any plant tissue.

The consensus genotyping methods may also be used to generate a consensus genotype for multiple specimens of any genetic material obtained from any source without departing from the steps disclosed.

EXAMPLE 1

Embryo Genotyping

A. Collection of Embryo Material:

Embryos were washed 3 times using 2 mL of sterile water. Embryos were incubated in a tube containing 10 µL, 20 µL, 50 µL 75 µL, or 150 µL of sterile water for 10 minutes, 20 minutes, or overnight. It was found that adequate genotyping data can be obtained with any of the dilution volumes, and that 10 minutes was a sufficient incubation time. All protocols for washing and incubating the embryos were used with all three tissue collection methods described below.

Method 1: The tubes containing the embryos were agitated via tapping 10 times and were then spun down in a tabletop centrifuge for 5 seconds. The water was then removed from each tube for analysis. It was found that this method achieved the best results for genotyping.

Method 2: Embryos were washed 3 times using 2 mL of sterile water. Embryos were incubated in a tube containing 50 µL of sterile water for 10 minutes. The water was then removed from the tube for analysis.

Method 3: Embryos were washed 3 times using 2 mL of sterile water. Embryos were incubated in a tube containing 50 µL of sterile water for 10 minutes.

Tubes containing the embryos were agitated via tapping 10 times. The water was then removed from each tube for analysis.

B. Methods to Obtain DNA:

Cold-Heat Shock:

Embryo material obtained using all three methods described above was placed in a −80° C. freezer for 20 min; then placed on a thermocycler at 100° C. for 10 min and pipetted up and down to mix. The process was repeated for a total of two rounds. The resulting mixtures were stored at −20° C. It was found that the best results for genotyping were achieved from DNA obtained using this method.

Heat Shock Only:

Embryo tissues were placed on a thermocycler at 100° C. for 10 min and pipetted up and down to mix. The process was repeated for a total of two rounds. The mixtures were stored at −20° C.

Enzymatic Method:

The mixtures from the preceding step were incubated in a 95° C. oven to evaporate off the remaining water. 18.0 µL of PBS solution and 2.0 µL of diluted VISCOZYME® L (commercially available from Sigma-Aldrich; diluted 1:200 in PBS Solution pH 7.4; total vol. 20 µL) were added and the mixtures were incubate at 37° C. for 2 hours. A quantity of 2.0 µL of diluted proteinase K (commercially available from Sigma-Aldrich; diluted 1:20 in PBS Solution pH 7.4) was added and the mixtures were incubated at 55° C. for 50 minutes then heated to 95° C. for 10 min. The mixtures were stored at −20° C.

DNA Extraction:

The mixtures from the methods of Example 1 B were incubated in a 95° C. oven to evaporate off the remaining water. 45 µL Lysis buffer PN (LGC Genomics) was added to each mixture, which were then centrifuged briefly and incubated at 65° C. for 1 hour. To new tubes were added 60 µL Binding buffer PN, 5 µL SBEADEX® particles (magnetic particles that bind genetic material, which are commercially available from LGC Genomics) followed by the lysate mixtures, which were then incubated at room temperature for 4 minutes to allow binding of DNA to the particles, vortexed briefly and placed in a magnetic rack to concentrate beads. The lysis buffer was removed and 100 µL wash buffer PN1 (LGC Genomics) were added to resuspend the beads. Washing was repeated using 100 µL wash buffer PN2 (LGC Genomics) followed by a 100 µL pure water wash. 10 µL elution buffer PN was added and the mixtures were incubated at 55° C. for 10 minutes with vortexing every 3 minutes. The magnetic rack was used to concentrate beads and the eluate was transferred to new tubes and stored at −20° C.

C. Whole Genome Amplification

When whole genome amplification was required the following protocol was followed using the REPLI-g® Single Cell Kit (commercially available from Qiagen). Whole genome amplification was done to achieve higher DNA yield and to facilitate the detection of high density marker sets.

2.5 µL template DNA was combined with 2.5 µL Buffer D1 (commercially available from Qiagen; total volume 5.0 µL) and incubated at room temperature for 3 minutes. 5.0 µL Buffer N1 (commercially available from Qiagen; total volume 10.0 µL) was added and the mixtures were vortexed and centrifuged briefly. A Master Mix containing 9.0 µL nuclease-free water, 29.0 µL REPLI-g® Reaction Buffer (commercially available from Qiagen) and 2.0 µL REPLI-g® DNA polymerase (commercially available from Qiagen) was used per reaction to give 50.0 µL total volume. The mixtures were run on a thermocycler using a 30° C. for 8 hours and 4° C. thereafter. DNA quantitation was performed using a QUBIT® assay (commercially available from Life Technologies). The DNA product was used directly in the genotyping step.

D. Molecular Analysis

TAQMAN® Marker Analysis

Marker analysis was carried out using TAQMAN® assays (commercially available from Life Technologies). DNA was diluted to a target concentration of 20 ng/µL. A 384 plate containing the DNA was loaded into LC480 real-time PCR thermocycler and run using the following program: pre-incubation: 1 cycle (95° C. for 5 minutes); amplification: 45 cycles, (−95° C. for 30 seconds, −60° C. for 45 seconds (single acquisition), −72° C. for 1 minute (single acquisition); cooling: 1 cycle, (−72° C. for 10 minutes, −40° C. for 30 seconds). Calls were read using Roche LC480 LIGHT-CYCLER® Software (commercially available from Roche Diagnostics).

Results

Figure 1:
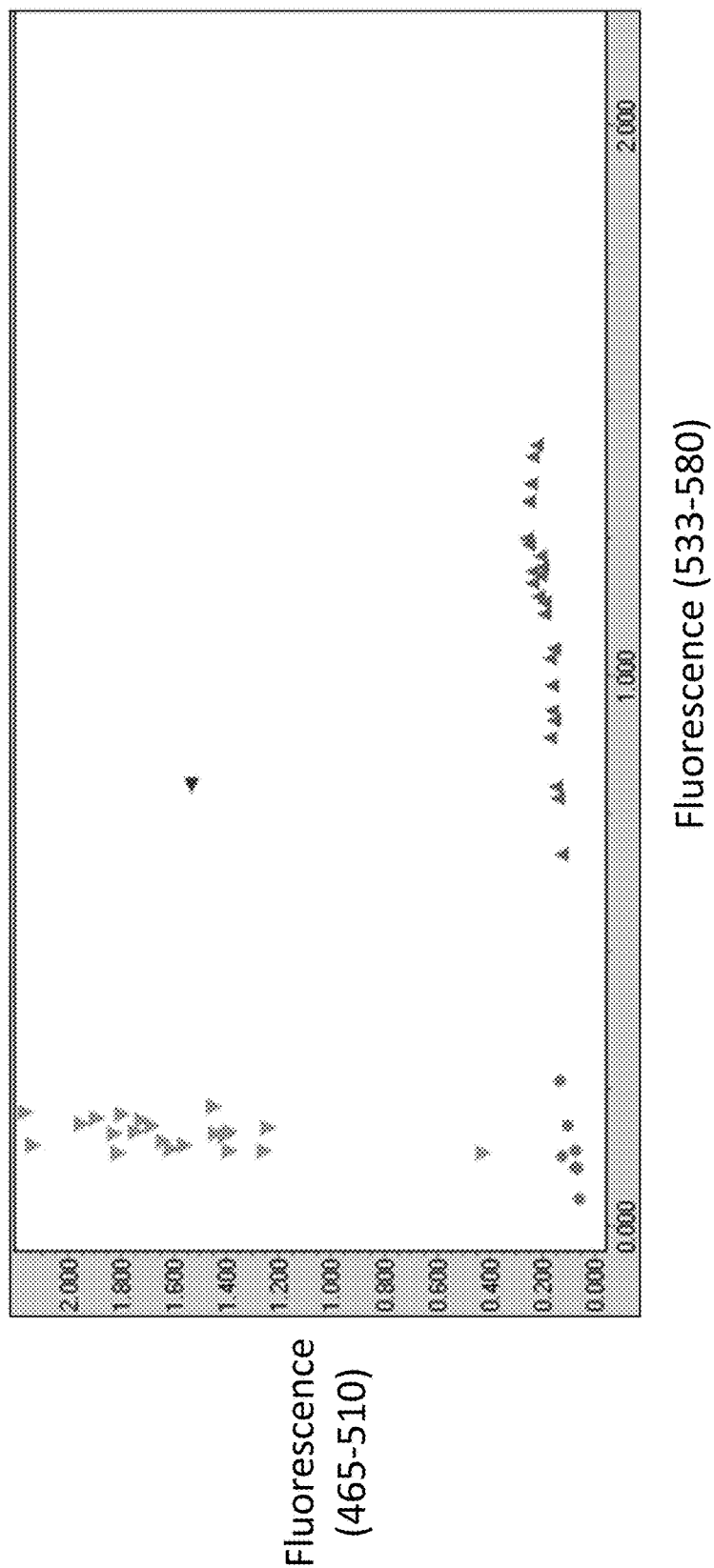
FIG. 1 depicts genotyping data from one marker using DNA obtained with the cold-heat shock treatment. The data represents three different treatments (incubate only; incubate and tap; and incubate, tap, and spin) in each of four different incubation volumes (10 µL, 20 µL, 50 µL, and 75 µL).
Figure 2:
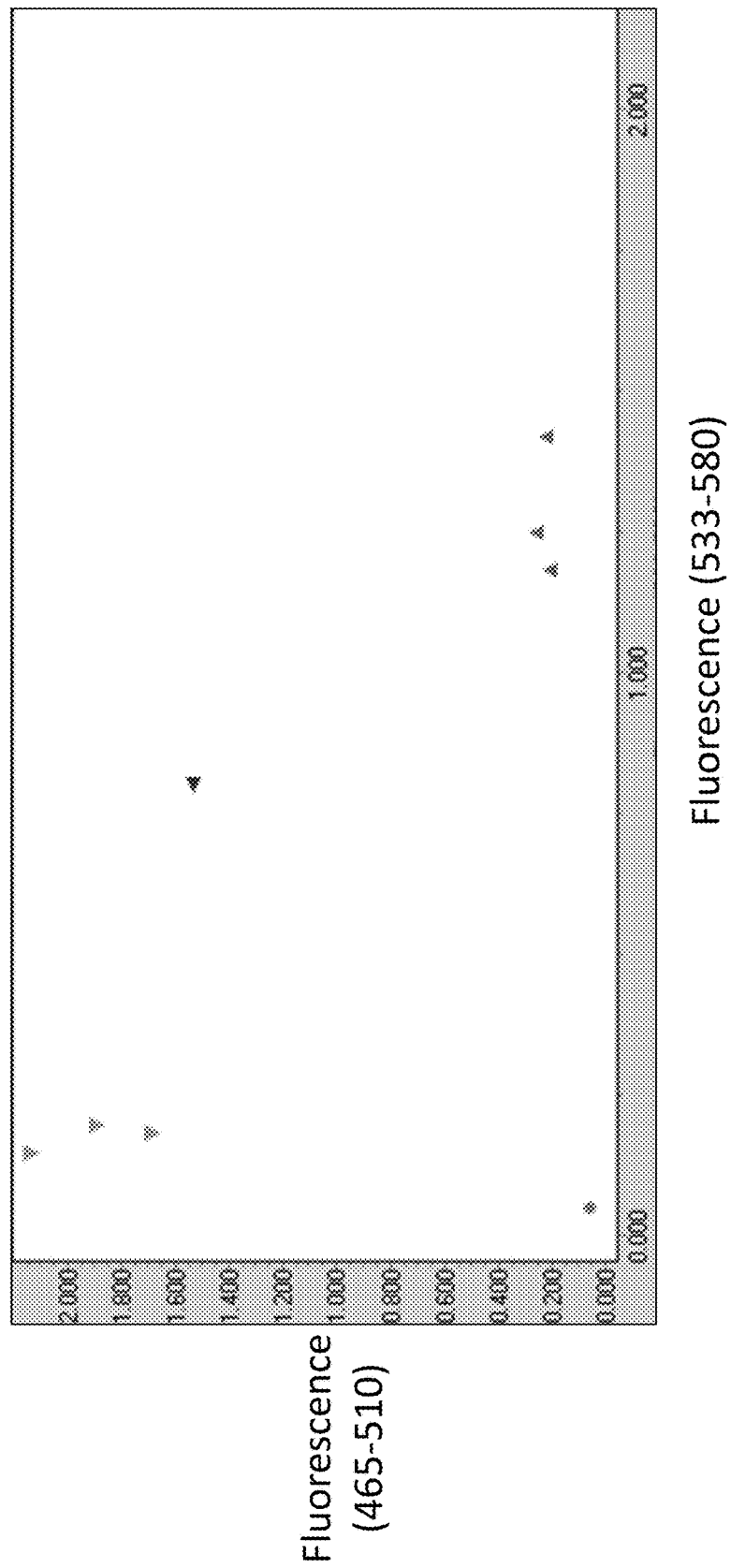
FIG. 2 depicts genotyping data from one marker using DNA obtained with the cold-heat shock treatment. The data represents one treatment (incubate, tap, and spin) in an incubation volume of 50 µL.
Figure 3:
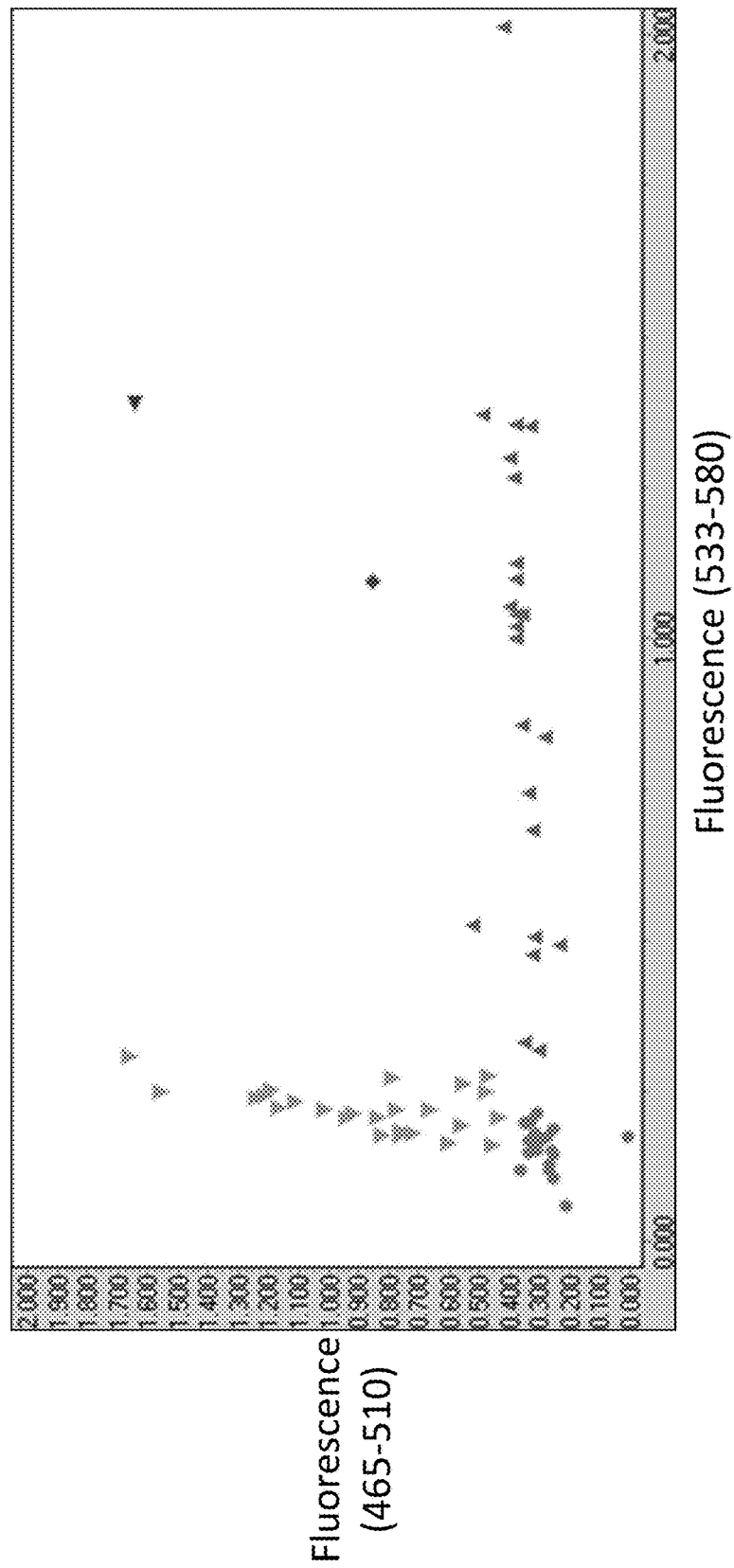
FIG. 3 depicts genotyping data from one marker using DNA obtained from cold-heat shock, heat shock, incubation with VISCOZYME® L, or DNA extraction using the SBEADEX® method. The data represents three different treatments (incubate only; incubate and tap; and incubate, tap, and spin) in an incubation volume of 50 µL.
Figure 4:
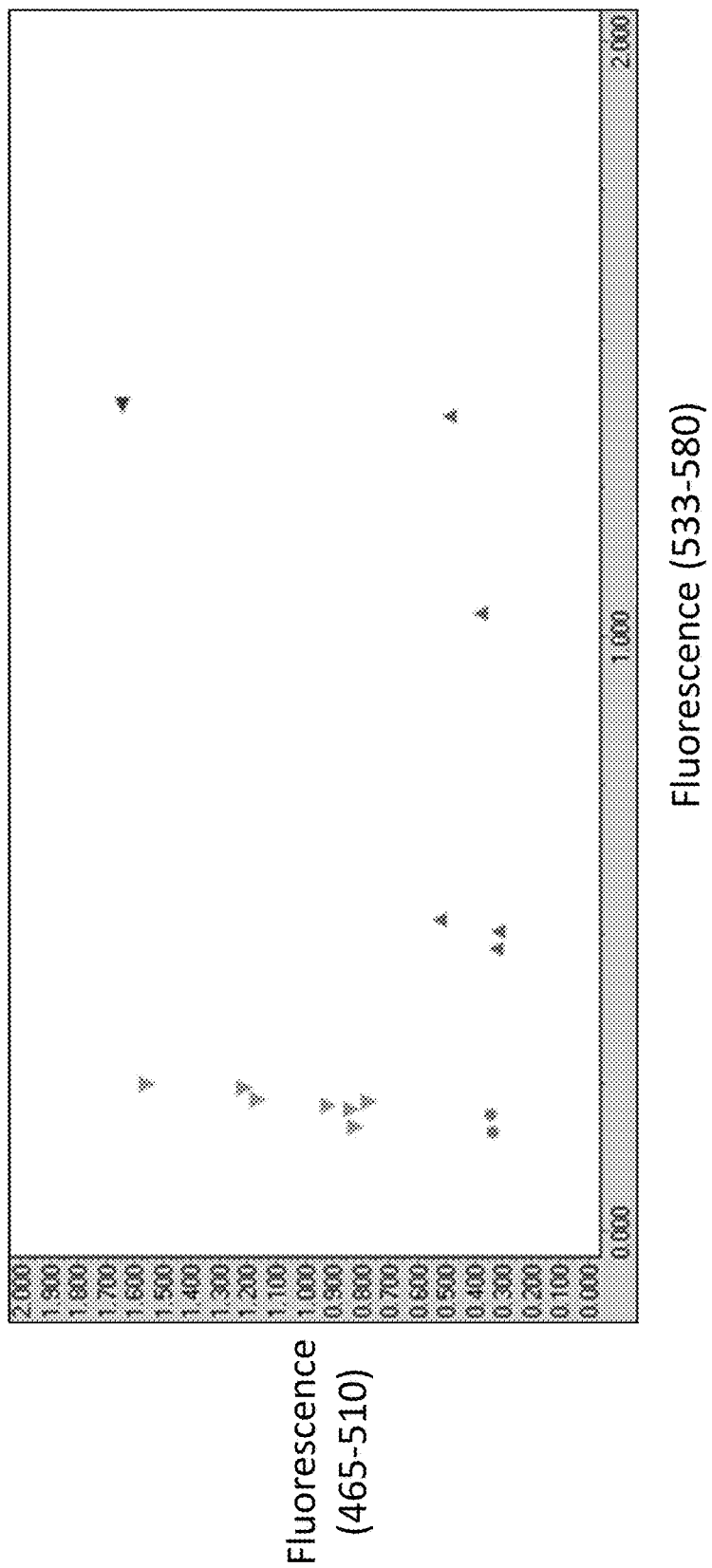
FIG. 4 depicts genotyping data from one marker using DNA obtained with the cold-heat shock treatment. The data represents one treatment (incubate, tap, and spin) in an incubation volume of 50 µL.
Figure 5:
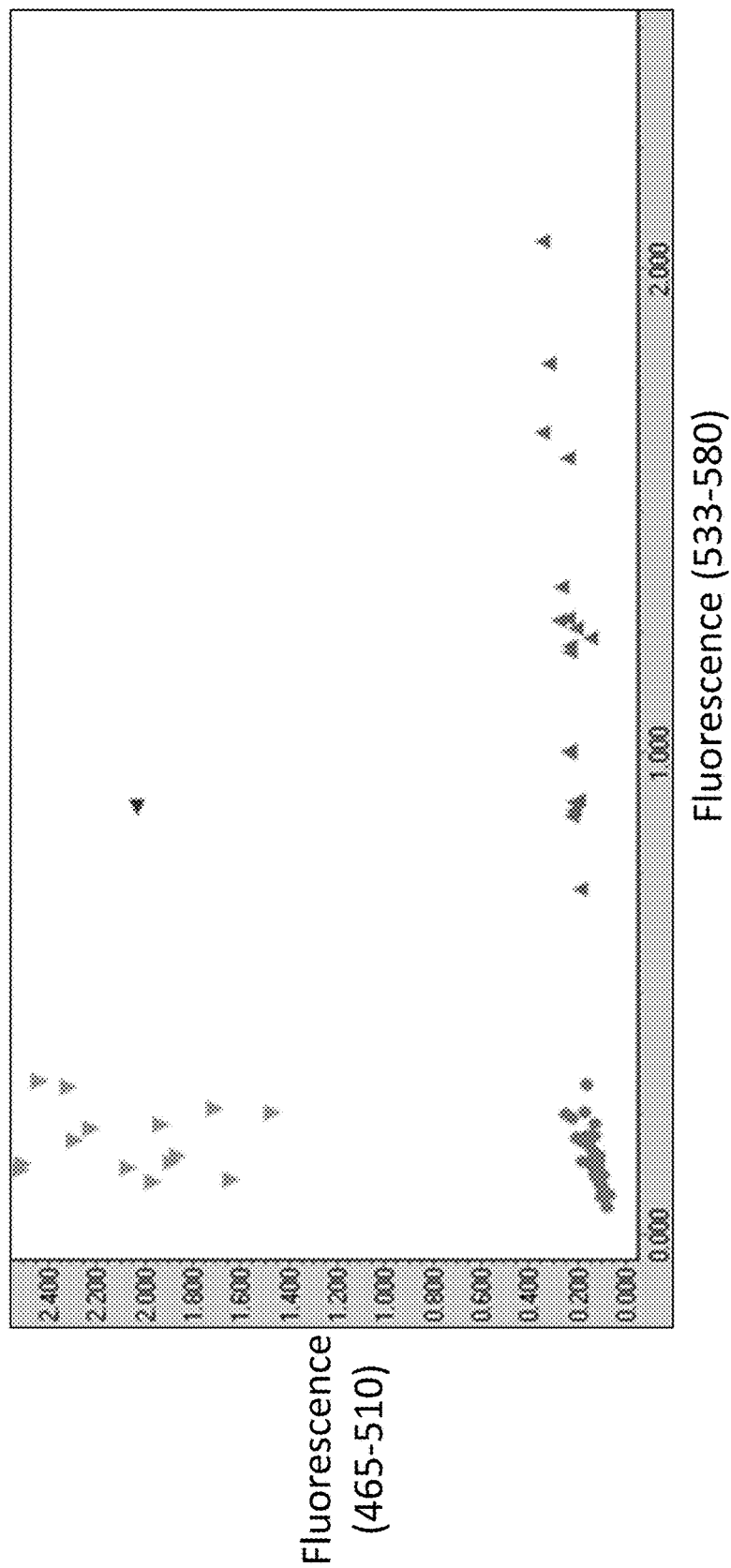
FIG. 5 depicts genotyping data from one marker using DNA obtained from cold-heat shock, incubation with VISCOZYME® L, or DNA extraction using the SBEADEX® method. The data represents three different treatments (incubate only; incubate and tap; and incubate, tap, and spin) in an incubation volume of 50 μL.
Figure 6:
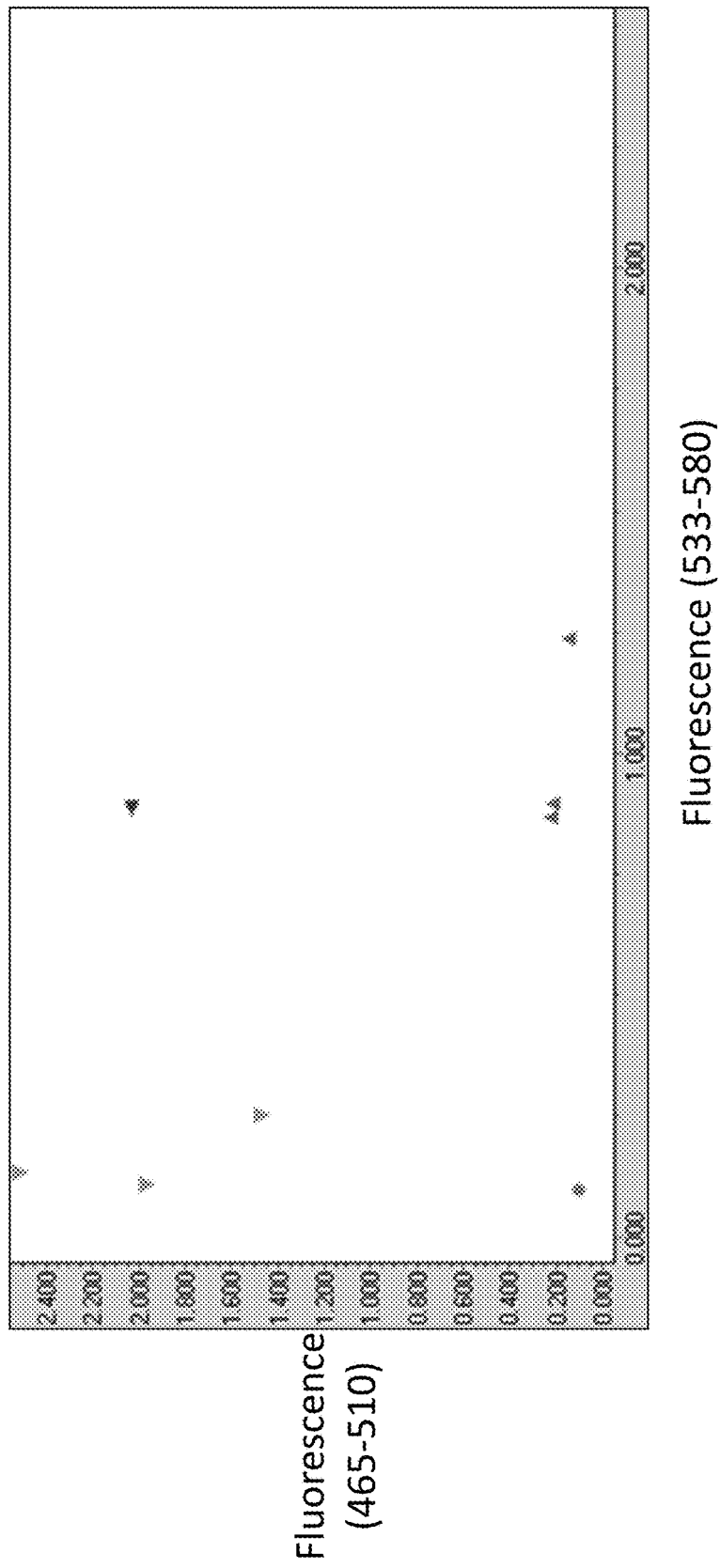
FIG. 6 depicts genotyping data from one marker using DNA obtained with the cold-heat shock treatment. The data represents one treatment (incubate, tap, and spin) in an incubation volume of 50 μL.
Figure 7:
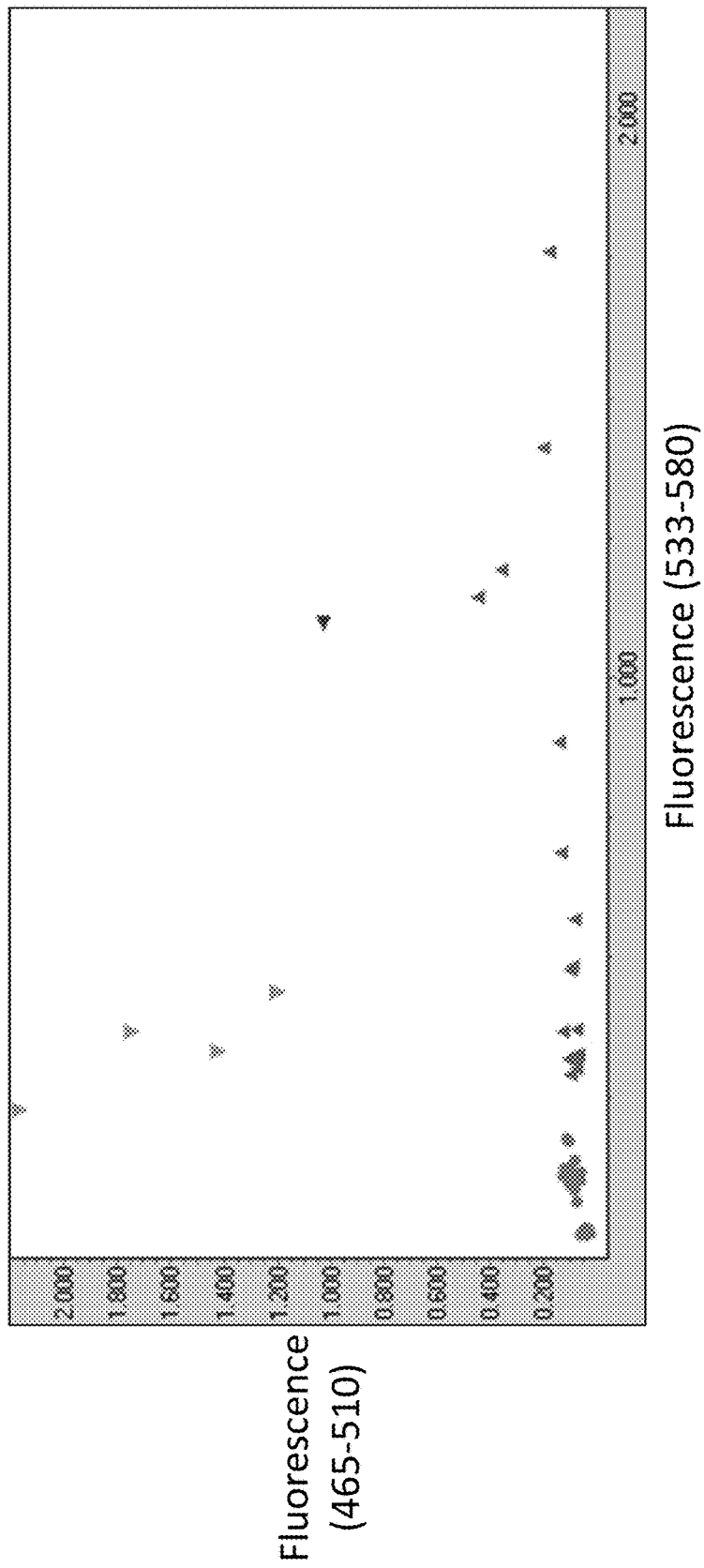
FIG. 7 depicts genotyping data from one marker using DNA obtained with the cold-heat shock treatment. The data represents three treatments (incubate only; incubate and tap; and incubate, tap, and spin) in an incubation volume of 150 μL.
Figure 8:
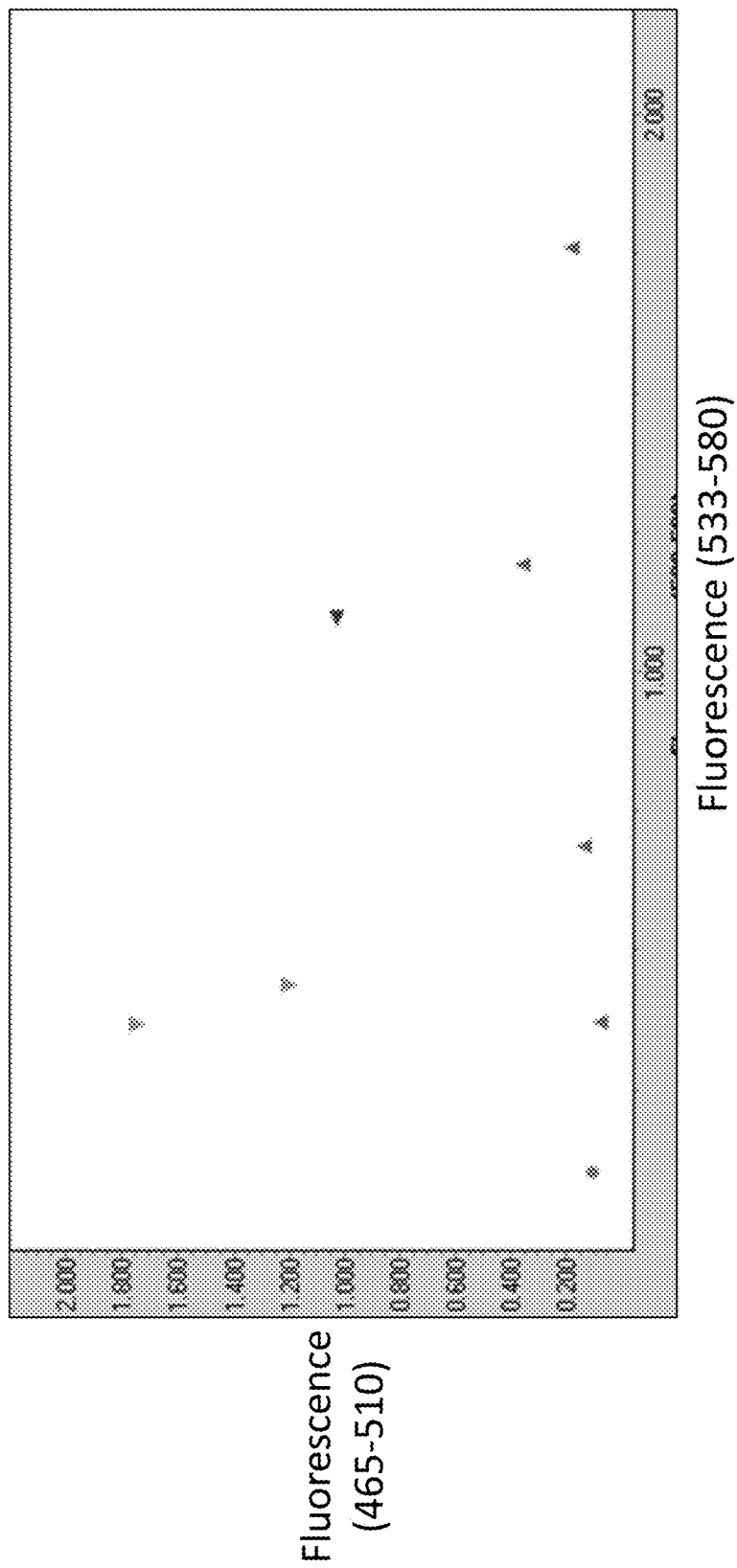
FIG. 8 depicts genotyping data from one marker using DNA obtained with the cold-heat shock treatment. The data represents one treatment (incubate, tap, and spin) in an incubation volume of 150 μL.
Figure 9:
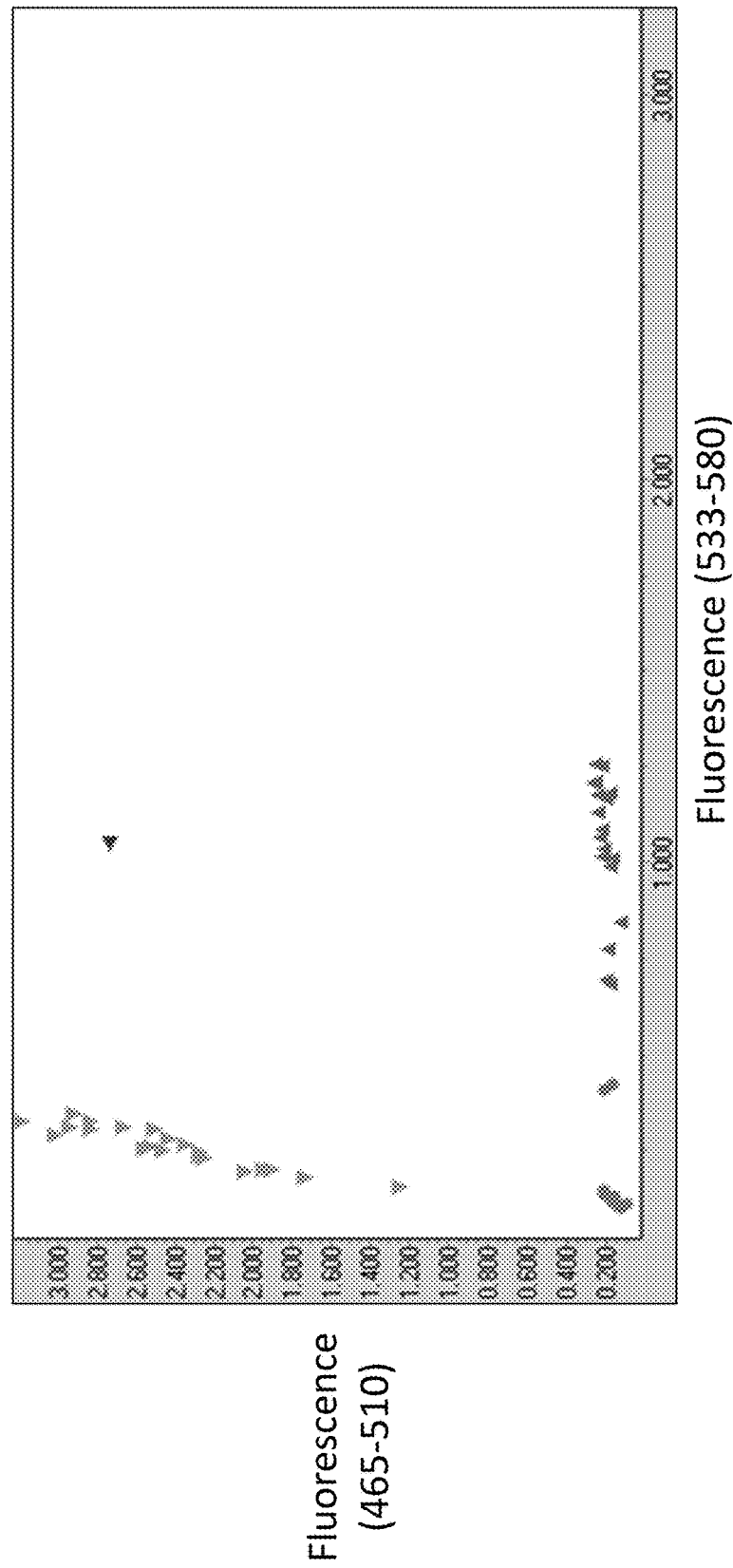
FIG. 9 depicts genotyping data from one marker using DNA obtained with the cold-heat shock treatment or no treatment at all following washing of the shed cellular material. The data represents three treatments (incubate only; incubate and tap; and incubate, tap, and spin) and two incubation volumes (50 μL and 100 μL).
Figure 10:
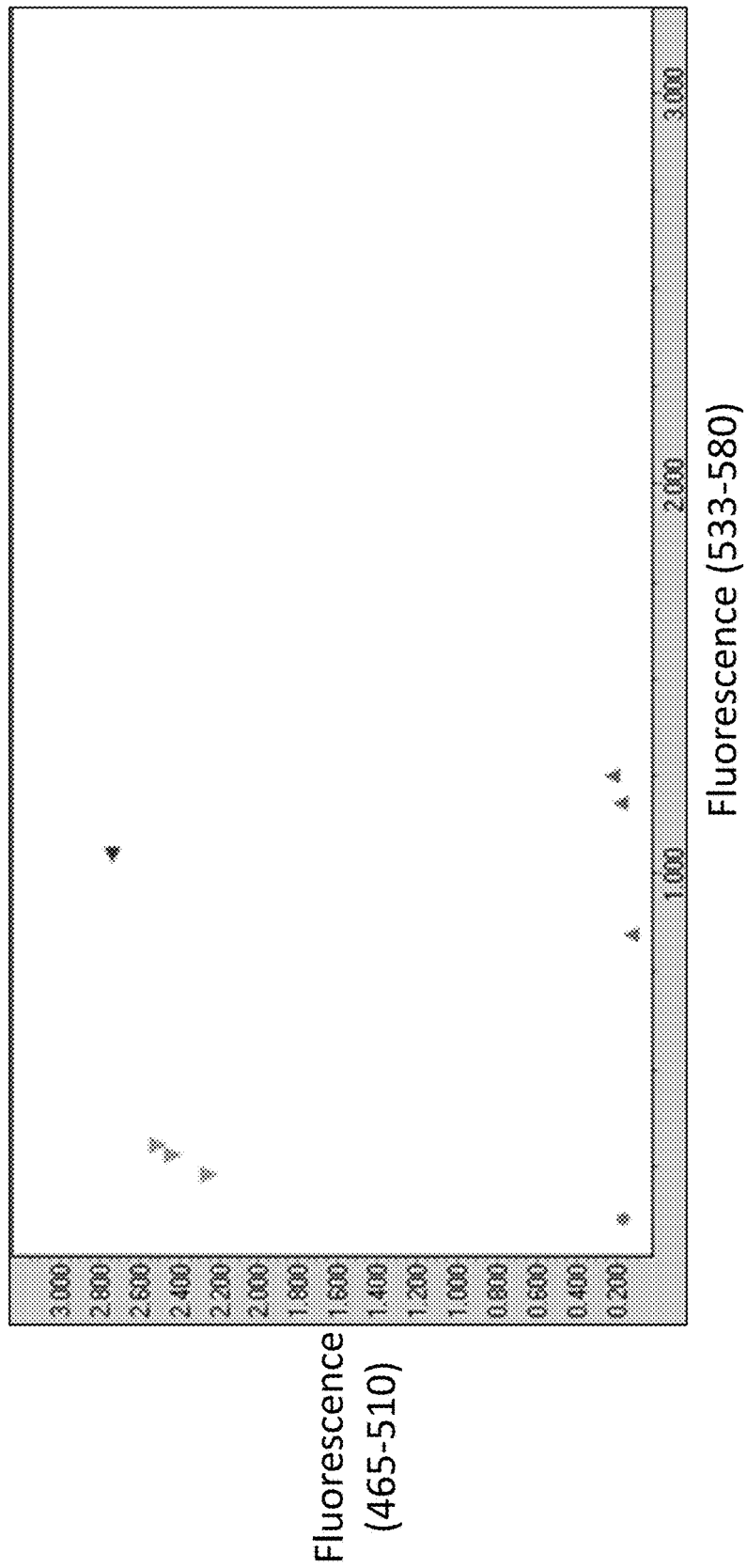
FIG. 10 depicts genotyping data from one marker using DNA obtained with the cold-heat shock treatment. The data represents one treatment (incubate, tap, and spin) in an incubation volume of 50 μL.

The foregoing methods all gave acceptable genotyping results. Genotypic data is shown in FIGS. 1-11, which include data from all permutations of the methods disclosed in this example. FIG. 1 depicts genotyping data from one marker using DNA obtained with the cold-heat shock treatment. The data represents three different treatments (incubate only; incubate and tap; and incubate, tap, and spin) in each of four different incubation volumes (10 µL, 20 µL, 50 µL, and 75 µL). FIG. 2 depicts genotyping data from one marker using DNA obtained with the cold-heat shock treatment. The data represents one treatment (incubate, tap, and spin) in an incubation volume of 50 µL. FIG. 3 depicts genotyping data from one marker using DNA obtained from cold-heat shock, heat shock, incubation with VISCO-ZYME® L, or DNA extraction using the SBEADEX® method. The data represents three different treatments (incubate only; incubate and tap; and incubate, tap, and spin) in an incubation volume of 50 µL. FIG. 4 depicts genotyping data from one marker using DNA obtained with the cold-heat shock treatment. The data represents one treatment (incubate, tap, and spin) in an incubation volume of 50 µL. FIG. 5 depicts genotyping data from one marker using DNA obtained from cold-heat shock, incubation with VISCO-ZYME® L, or DNA extraction using the SBEADEX® method. The data represents three different treatments (incubate only; incubate and tap; and incubate, tap, and spin) in an incubation volume of 50 µL. FIG. 6 depicts genotyping data from one marker using DNA obtained with the cold-heat shock treatment. The data represents one treatment (incubate, tap, and spin) in an incubation volume of 50 µL. FIG. 7 depicts genotyping data from one marker using DNA obtained with the cold-heat shock treatment. The data represents three treatments (incubate only; incubate and tap; and incubate, tap, and spin) in an incubation volume of 150 µL. FIG. 8 depicts genotyping data from one marker using DNA obtained with the cold-heat shock treatment. The data represents one treatment (incubate, tap, and spin) in an incubation volume of 150 µL. One of the homozygous calls was incorrect. FIG. 9 depicts genotyping data from one marker using DNA obtained with the cold-heat shock treatment or no treatment at all following washing of the shed cellular material. The data represents three treatments (incubate only; incubate and tap; and incubate, tap, and spin) and two incubation volumes (50 µL and 100 µL). FIG. 10 depicts genotyping data from one marker using DNA obtained with the cold-heat shock treatment. The data represents one treatment (incubate, tap, and spin) in an incubation volume of 50 µL. FIG. 11 depicts genotyping data from one marker using DNA obtained with the cold-heat shock treatment and whole genome amplification (using the REPLI-g Single Cell Kit) to obtain sufficient yield of DNA prior to genotyping. The data represents four treatments (incubate only; vortex at speed 3 for 5 seconds; vortex at speed 10 for 5 seconds; and vortex at speed 10 for 30 seconds) in an incubation volume of 10 µL.

EXAMPLE 2

Embryo Storage

Two lines of maize germplasm were selected for testing the impacts of extended embryo storage in an oil matrix on germination rates. Embryos from each line were isolated by hand before being placed into their respective storage condition. All embryos were plated on germination media to evaluate germination rates in a controlled growth chamber. Six embryos of each line were immediately plated on germination media without any storage exposure to act as a control for germination in a controlled growth chamber. Seventy two (72) embryos of each line were isolated and evenly divided across three storage conditions, with a dedicated storage tube for each embryo:

Storage condition 1: 24 embryos were placed in 50 µL aqueous solution surrounded by two layers of oil with significantly different densities, one with a density significantly greater than water and one with a density significantly less than water.

Storage condition 2: 24 embryos were placed in a 50 µL droplet of aqueous solution with an added antimicrobial agent, surrounded by the two oils of condition 1.

Storage condition 3: 24 embryos were placed in a 50 µL droplet of minimal growth media with an added antimicrobial agent, surrounded by the two oils of condition 1.

All tubes were placed in a dark refrigerator at 4 degrees centigrade for the duration of the experiment. At four (4) time points, 6 embryos of each line were removed from their storage condition and plated on germination media in a controlled growth chamber to evaluate germination rates. The time points were as follows:

Time point 1: 15 minutes after placement into storage.
Time point 2: 1 day after placement into storage.
Time point 3: 5 days after placement into storage.
Time point 4: 10 days after placement into storage.

Embryo germination rates were then monitored to determine optimal storage conditions. The results of these tests are shown in FIGS. 12 and 13 (results for two different lines of maize). It was found that germination rates were excellent in each of the three storage methods.

EXAMPLE 3

Pericarp Genotyping

A. Pericarp Peeling

Kernels of corn were removed from the cob and soaked for 60 minutes in deionized water. A scalpel blade was sterilized using a bead sterilizer. The scalpel was used to cut the back side of the seeds (away from the embryo) near the tips, as shown in FIG. 14*a*. The scalpel was again sterilized using a bead sterilizer and cooled in sterile water. The scalpel was then used to cut along the outer edge of the kernel, as shown in FIG. 14*b*. Forceps were sterilized in a bead sterilizer, cooled, and then used to peel the pericarp from the kernel, as shown in FIG. 14*c*. The pericarp tissue from each kernel was then placed in microcentrifuge tubes.

B. Pericarp Washing

Three different washing solutions were tested. The best results were achieved washing with 1% sodium dodecyl sulfate (SDS) solution, although adequate results were achievable using water and ethanol. An alternative washing method using sonication also gave adequate results. The washing protocol used began by adding 1 mL wash solution to the microcentrifuge tubes, which was placed in an inverter for 1 minute. The wash solution was removed and replaced with 1 mL fresh wash solution, then the microcentrifuge tubes were again placed in an inverter, this time for 4 minutes. The pericarp tissue was then removed, rinsed with distilled water, and placed into a new microcentrifuge tube. The sonication protocol placed the pericarp tissue in a sonicator for 1 minute. The tissue was then removed, rinsed with distilled water, and placed in a fresh microcentrifuge tube.

C. Obtaining DNA

Five methods for obtaining DNA were tested. The best results were achieved with the gentleMACS™ protocol with water or TE supernatants.

gentleMACS™/Water or TE supernatants: In this method, pericarp tissue was placed directly onto the rotor of a gentleMACS™ M tube. 300 ul of water or TE buffer was added to the tube, which was then closed and placed in a gentleMACS™ machine. The automated program "Protein_01.01" was run. For pericarp tissues that were not fully dissociated, further mixing and running of the automated program was done. Next, the mixtures were spun down in the GentleMACS™ tube and transferred to a new 1.5 ml Eppendorf tube. The Eppendorf tube was then centrifuged at 14000 rpm for 2 minutes, and the supernatant were transferred to a fresh 1.5 ml Eppendorf tube for the molecular analysis. No extraction of DNA was required in this method.

GentleMACS™/SBEADEX® In this method, pericarp tissue was placed directly onto the rotor of a gentleMACS™ M tube. 300 µL of SBEADEX® Lysis Buffer PN was added to the tube, which was then closed and placed in a gentleMACS™ machine. The automated program "Protein_01.01" was run. For pericarp tissues that were not fully dissociated, further mixing and running of the automated program was done. Next, the mixtures were centrifuged and incubated at 65° C. for 1 hour with occasional agitation. 360 µL of Binding Buffer PN and 30 µL SBEADEX® particles were added to fresh 1.5 mL Eppendorf tubes. The tubes with the pericarp tissue were centrifuged and the lysate was transferred to the fresh tubes. These were then incubated at room temperature for 4 minutes to allow the DNA to bind to the SBEADEX® particles. The tubes were then vortexed briefly then placed in a magnetic rack to concentrate the beads. The lysis buffer was removed and 600 µL of wash buffer PN1 was added to each tube and the beads were resuspended. The tubes were again placed in a magnetic rack to concentrate the beads and the wash buffer PN1 was removed. This washing procedure was repeated using 600 µL of wash buffer PN2, then repeated again using 600 µL of pure water. Following this third washing step, 40 µL of elution buffer PN was added and the tubes were incubated at 55° C. for 20 minutes and vortexed every 3 minutes. A magnetic plate was used to concentrate the beads, and the eluate was transferred into fresh tubes, and then stored at −20° C. until molecular characterization.

gentleMACS™/Extract-N-Amp™: In this method, pericarp tissue was again placed directly onto the rotor of a gentleMACS™ M tube. 300 µL of sterile water was added to the tube, which was then closed and placed in a gentleMACS™ machine. The automated program "Protein_01.01" was run. For pericarp tissues that were not fully dissociated, further mixing and running of the automated program was done. The homogenate was transferred to a 1.5 mL microcentrifuge tube and centrifuged for 1 minute at 10,000 rpm. The supernatant was removed without disturbing the tissue pellet at the bottom of the tube. 30 µL of Extraction Solution/Seed Preparation Solution mix (Sigma-Aldrich Extract-N-Amp™ Seed PCR kit) was added and the resulting mixture was thoroughly mixed. The mixture was transferred to PCR strip tubes for use on the thermocycler, which was programmed to hold 55° C. for 10 minutes, then 95° C. for 3 minutes, then to hold 4° C. indefinitely. 30 µL of Neutralization Solution B was added.

Liquid Nitrogen/SBEADEX®: 1.5 mL microcentrifuge tube pestles were placed in liquid nitrogen to cool. Pericarp tissue was placed in microcentrifuge tubes along with the cooled pestles and the entire tube was placed in liquid nitrogen. Liquid nitrogen was added to the tubes. The pericarp tissue was ground slowly and thoroughly using the pestle. The tubes were occasionally dipped back into the liquid nitrogen to keep the tissue cold. After grinding, 90 µL of Lysis buffer PN was added to each tube, which was then briefly centrifuged then incubated at 65° C. for 1 hour. 120 µL of binding buffer PN and 10 µL of SBEADEX® particles were added to fresh tubes, and the lysate from the grinding step was added to the new tubes. These were then incubated at room temperature for 4 minutes to allow the DNA to bind to the SBEADEX® particles. The mixtures were then briefly vortexed and placed in a magnetic rack to concentrate the beads. The lysis buffer was removed and 200 µL of wash buffer PN1 was added to each tube and the beads were resuspended. The tubes were again placed in a magnetic rack to concentrate the beads and the wash buffer PN1 was removed. This washing procedure was repeated using 200 µL of wash buffer PN2, then repeated again using 200 µL of pure water. Following this third washing step, 20 µL of elution buffer PN was added and the tubes were incubated at 55° C. for 10 minutes and vortexed every 3 minutes. A magnetic plate was used to concentrate the beads, and the eluate was transferred into fresh tubes, and then stored at −20° C. until molecular characterization.

Extract-N-Amp™: A master mix of 18 parts extraction solution and 2 parts of seed preparation solution was made and 20 µL of the solution added to pericarp tissue in 0.2 mL PCR strip tubes. The mixtures were placed in a thermocycler set at 55° C. for 10 minutes, 95° C. for 3 minutes, then 4° C. indefinitely. 20.0 µL of Neutralization Solution B was added and the liquid portion of the mixture was transferred to fresh 1.5 mL microcentrifuge tubes.

D. Molecular Testing

QUBIT® dsDNA HS Assay Kit: QUBIT® reagent was diluted into QUBIT® buffer at a 1:200 ratio to make a working solution. 1 µL of the PCR products of step 2B was transferred to 0.5 mL QUBIT® assay tubes and 199 µL of the working solution. Standards were made by adding 10 µL of standard to 190 µL of QUBIT® working solution. The PCR products and standards were vortexed for 2-3 seconds then briefly centrifuged. The tubes were then incubated at room temperature for 2 minutes. The tubes were then inserted into a QUBIT® 2.0 fluorometer and readings were recorded.

Whole Genome Amplification (Seqplex): The preferred method of whole genome amplification is the Seqplex method using the Seqplex Enhanced DNA Amplification Kit. To 1 µL of each DNA solution generated in step C was added 2 µL library preparation buffer and 11 µL pure water. The solution was centrifuged, vortexed, and centrifuged again, incubated on a thermocycler at 95° C. for 2 minutes, then held at 4° C. After cooling, 1 µL of library preparation enzyme was added. The solution was centrifuged, vortexed, and centrifuged again, then incubated on a thermocycler at 16° C. for 20 minutes, 24° C. for 20 minutes, 37° C. for 20 minutes, 75° C. for 5 minutes, then held at 4° C. The solution was the briefly centrifuged. 15 µL of this solution was added to 15 µL of 5× Amplification Mix (A5112), 1.5 µL DNA Polymerase for SeqPlex (SP300), 42.5 µL sterile water (W4502) and 1 µL SYBR Green (S9403), diluted 1:1000. This solution was mixed thoroughly, and each reaction mix was divided into five 15 µL aliquots on a 384 well plate. The amplification thermocycle began with an initial denaturation at 94° C. for 2 minutes followed a sufficient number of cycles to reach 2-3 cycles into the plateau (typically about 24 cycles): 94° C. denature for 15 seconds, 70° C. anneal/extend for 5 minutes, read fluorescence, repeat. After cycling, the reaction mix was held at 70° C. for 30 minutes then held at 4° C. After cooling, the samples were purified via QIAQUICK® PCR purification.

Whole Genome Amplification (REPLI-g Single Cell Kit): Denaturation buffer D1 was prepared by adding 3.5 µL of reconstituted buffer DLB and 12.5 nuclease-free water. Neutralization buffer N1 was prepared by adding 4.5 µL of stop solution and 25.5 µL of nuclease-free water. 2.5 µL of the denaturation buffer was added to each 2.5 µL aliquot of DNA solution prepared in step C. This solution was incubated at room temperature for 3 minutes. 5.0 µL of the neutralization buffer N1 was added, and the solution was vortexed then centrifuged briefly. A master mix was prepared with 9.0 μL nuclease-free water, 29.0 μL of REPLI-g reaction buffer, and 2.0 μL of REPLI-g DNA polymerase per reaction. 40.0 μL of this master mix was added to each solution, which is then run on a thermocycler at 30° C. for 8 hours, then cooled to 4° C.

The whole genome amplification products were evaluated using the QUBIT® assay to determine yield of DNA.

Genotyping Assays. Both high density markers (the ILLUMINA® 3072X chip) and TAQMAN® marker analysis were successfully employed to genotype the genetic materials described in this example. Data demonstrating the effectiveness of the foregoing techniques is presented in FIGS. 2-4. FIG. 15 compares the data quality obtained using DNA extraction methods against that obtained using whole genome amplification. While both methods give acceptable results, the whole genome amplification method gives preferable results, with each of the three haplotypes well-resolved. FIG. 16 is a fluorescent marker scatter plot demonstrating that quality fluorescent marker data can be obtained from a single pericarp tissue sample. In fact, the methods of the invention allow genotyping using many markers, tens or potentially hundreds, using pericarp tissue extracted from a single seed. FIG. 17 demonstrates the reliability of the methods of the invention because of the high degree of similarity between the measured genotype of the pericarp tissue extracted from a single seed (each line) and the known maternal genotype.

EXAMPLE 4

Genotyping Using Agar Medium

Embryos were isolated and cultured on colchicine agar medium for doubling treatment. After 24 hours, diploid embryos present purple color; and haploid embryos present white color. White embryos were then transferred to plates for continued growth. Using a sterilized spatula, a portion of agar media (slightly larger than the embryo itself) was scooped from directly beneath the embryo from the initial 24-hour doubling plate. The portion of agar was transferred to a 2.0 mL tube containing 60 μL sterile TE buffer. The tube was incubated for 10 minutes at room temperature, vortexed at the highest speed for 5 seconds, and centrifuged for 10 seconds in a tabletop centrifuge. Approximately 60 μL of liquid was transferred to a PCR strip tube. PCR strip tubes were placed in a −80° C. freezer for 20 minutes and then placed in a thermocycler at 100° C. for 10 minutes followed by a 4° C. hold. The tubes were vortexed, and the cold-heat shock treatment was repeated a second time. TAQMAN® marker analysis was successfully employed to genotype genetic material obtained from shed cellular material of the doubled haploid embryos, in which the shed cellular material was obtained from the agar medium. Results were comparable to genotyping calls obtained from embryo tissue of the doubled haploid embryo with the hotshot DNA extraction method. Genotyping of the doubled haploid embryo using shed cellular material contained within or on agar medium was successful.

EXAMPLE 5

Germination and Maturation Test

Shed cell materials were collected from doubled haploid embryos contained within a non-destructive medium using one of four agitation treatments (tapping, exposure to linear vibrations, vortexing, and use of pneumatic piston) as well as no agitation. The doubled haploid embryos from which the shed cellular material obtained were then evaluated for germination and maturation abilities. The embryos were germinated on medium for 11 days, and then transferred to the greenhouse for a continued growth and maturation, in order to confirm that the collection methods had not caused any adverse effects on long-term plant development. The plants were self-pollinated, and doubled haploid phenotypes, e.g. kernel coloration and plant height, were observed. Images of the plants and self-pollinated ears were collected. Leaf tissue was also collected from each plant using a leaf puncher. The genotypic data obtained from the shed cellular material of the doubled haploid embryos corresponded to the genotypic data obtained from the leaf tissue. Thus, the plants that developed from the doubled haploid embryos germinated and matured normally with no appearance of adverse effects arising from agitation of the embryos to release shed cellular material.

EXAMPLE 6

Genotyping of Microspore-derived Embryonic Tissue

Embryonic tissue derived from microspores was transferred from a growth plate to a 1.5 mL tube containing 40 μL of sterile TE buffer using a sterilized spatula. The microspore-derived embryonic tissue was incubated for 30 minutes at room temperature. In one set of experiments, the tubes were placed on a pneumatic piston arm, which subjected the microspore-derived embryonic tissue to lateral motion. In another set of experiments, the tubes were vortexed at high speeds for 10 seconds. After agitation, the tubes were then centrifuged for 10 seconds in a tabletop centrifuge, and ~40 μL of liquid was transferred to a PCR strip tube. The tubes containing the non-destructive medium were placed in a −80° C. freezer for 20 minutes and then placed in a thermocycler at 100° C. for 10 minutes followed by 4° C. hold. The tubes were vortexed, and the cold-heat shock-agitation cycle was repeated. Four markers were used for genotyping, which showed that shed cellular material obtained from microspore-derived embryonic tissue could successfully be used for genotyping.

We claim:
1. A method of selecting an ungerminated maize embryo to grow into a plant comprising:
   (a) obtaining portions of agar in contact with multiple ungerminated maize embryos, wherein each of said portions comprise shed cellular material of one of said multiple ungerminated maize embryos;
   (b) obtaining genetic material from at least one portion of agar comprising the shed cellular material;
   (c) performing molecular analyses of the genetic material obtained from the at least one portion of agar comprising shed cellular material;
   (d) selecting an ungerminated maize embryo based on the molecular analysis performed in step (c) to generate a selected ungerminated maize embryo; and
   (e) germinating the selected ungerminated maize embryo into a plant.
2. The method of claim 1, wherein said agar comprises a chromosome doubling agent.
3. The method of claim 2, wherein said chromosome doubling agent is colchicine.

4. The method of claim 1, further comprising removing at least one ungerminated maize embryo from the agar and storing said maize embryo.

5. The method of claim 1, wherein said molecular analysis is genotyping.

6. The method of claim 1, wherein the multiple ungerminated maize embryos are removed from the agar using an automated process.

* * * * *